US012790338B2

(12) United States Patent
Anderson et al.

(10) Patent No.: US 12,790,338 B2
(45) Date of Patent: Nov. 10, 2026

(54) PRPK INHIBITORS

(71) Applicant: Dana-Farber Cancer Institute, Inc., Boston, MA (US)

(72) Inventors: Kenneth C. Anderson, Wellesley, MA (US); Teru Hideshima, Brookline, MA (US); Sirano Dhe-Paganon, Dorchester, MA (US); Hyuk-Soo Seo, Boston, MA (US); Takashi Mizutani, Ibaraki (JP); Tinghu Zhang, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 686 days.

(21) Appl. No.: 18/013,106

(22) PCT Filed: Jun. 28, 2021

(86) PCT No.: PCT/US2021/039358

§ 371 (c)(1),
(2) Date: Dec. 27, 2022

(87) PCT Pub. No.: WO2022/005961

PCT Pub. Date: Jan. 6, 2022

(65) Prior Publication Data

US 2023/0271966 A1 Aug. 31, 2023
US 2024/0124459 A9 Apr. 18, 2024

Related U.S. Application Data

(60) Provisional application No. 63/045,745, filed on Jun. 29, 2020.

(51) Int. Cl.

*C07D 487/04* (2006.01)
*A61P 35/00* (2006.01)
*C07D 401/04* (2006.01)
*C07D 413/14* (2006.01)

(52) U.S. Cl.

CPC ............ *C07D 487/04* (2013.01); *A61P 35/00* (2018.01); *C07D 401/04* (2013.01); *C07D 413/14* (2013.01)

(58) Field of Classification Search

None
See application file for complete search history.

(56) References Cited

U.S. PATENT DOCUMENTS

| | | | |
|---|---|---|---|
| 4,522,811 | A | 6/1985 | Eppstein et al. |
| 2002/0155166 | A1 | 10/2002 | Choi et al. |
| 2011/0319277 | A1 | 12/2011 | Park et al. |
| 2017/0356917 | A1 | 12/2017 | Hideshima et al. |

FOREIGN PATENT DOCUMENTS

| | | |
|---|---|---|
| WO | WO 2018/148440 | 8/2018 |
| WO | WO 2018/200981 | 11/2018 |
| WO | WO 2019/148055 | 8/2019 |

OTHER PUBLICATIONS

International Preliminary Report on Patentability in International Application No. PCT/US2021/039358, mailed on Jan. 12, 2023, 7 pages.
Hideshima et al., "p53-related protein kinase confers poor prognosis and represents a novel therapeutic target in multiple myeloma," Blood, Mar. 2017, 129(10):1308-1319.
International Search Report and Written Opinion in International Application No. PCT/US2021/039358, mailed on Dec. 6, 2021, 10 pages.
Murray et al., "Small-molecule p21-activated kinase inhibitor PF-3758309 is a potent inhibitor of oncogenic signaling and tumor growth," PNAS, May 2010, 107(20):9446-9451.
Ferguson M.H., et al., "Reliability of Scientific Data", Journal of Pharmaceutical Sciences, vol. 66, No. 2, Feb. 1977, Title page, and Copyright p. 1 Page.
Gennaro A.R., "Remington's Pharmaceutical Sciences", 17th edition, Mack Publishing Company, Easton, Pa., 1985, Title page, Copyright page, Table of Contents, and p. 1418, 4 Pages.
Greene T.W., et al., "Protective Groups in Organic Synthesis", 3rd Edition, John Wiley & Sons, Inc., New York (1999), Title page, Copyright page, and Table of Contents, 4 Pages.

*Primary Examiner* — Kortney L. Klinkel
(74) *Attorney, Agent, or Firm* — Mueting Raasch Group

(57) ABSTRACT

This disclosure relates to compounds of formula (I) as defined in the Specification. This disclosure also relates to methods of synthesizing the compound of formula (I) and using the compounds of formula (I) for treating a disease (e.g., cancer).

14 Claims, No Drawings

PRPK INHIBITORS

CROSS-REFERENCE TO RELATED APPLICATIONS

The present application is a U.S. national phase filing under 35 U.S.C. § 371 of International Application No. PCT/US2021/039358, filed Jun. 28, 2021, which claims priority to U.S. Provisional Application Ser. No. 63/045,745, filed on Jun. 29, 2020, the contents of which are hereby incorporated by reference in their entirety.

TECHNICAL FIELD

This disclosure relates to PRPK inhibitors, as well as methods of synthesizing and using such compounds.

BACKGROUND p53-related protein kinase (TP53RK, also known as PRPK) is an upstream kinase that phosphorylates (serine residue Ser15) and mediates p53 activity. Studies have shown that TP53RK confers poor prognosis in multiple myeloma (MM) patients, and, conversely, that TP53RK knockdown inhibits p53 phosphorylation and triggers MM cell apoptosis, associated with downregulation of c-Myc and E2F-1-mediated upregulation of pro-apoptotic Bim. It has also been demonstrated that TP53RK downregulation also triggers growth inhibition in p53-deficient and p53-mutant MM cell lines and that downstream targets of TP53RK include ribonucleotide reductase-1, telomerase reverse transcriptase, and cyclin-dependent kinase inhibitor 2C.

SUMMARY

This disclosure is based on the unexpected discovery of certain compounds can inhibit PRPK activities and therefore can be used as PRPK inhibitors for treating cancers (e.g., multiple myeloma).

In one aspect, this disclosure features a compound of formula (I) or a salt thereof:

(I)

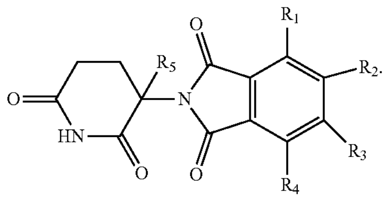

In formula (I), each of $R_1$, $R_2$, $R_3$, and $R_4$, independently, is H, halo, OR, COOR, C(O)R, C(O)N(RR'), NH—S(O)$_2$—R, N(RR'), $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_1$ and $R_2$, together with the carbon atoms to which they are attached, form a group comprising a five-membered or six-membered ring; or $R_2$ and $R_3$, together with the carbon atoms to which they are attached, form a group comprising a five-membered or six-membered ring; or $R_3$ and $R_4$, together with the carbon atoms to which they are attached, form a group comprising a five-membered or six-membered ring; $R_5$ is H or $C_1$-$C_{10}$ alkyl optionally substituted by aryl; each of $C_1$-$C_{10}$ arylalkyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, five-membered ring, and six-membered, independently, is optionally substituted by $C_1$-$C_{10}$ alkyl, halo, OR, or COOR; and each of R and R', independently, is H, $C_1$-$C_{10}$ alkyl, $C_3$-$C_{20}$ cycloalkyl, $C_3$-$C_{20}$ heterocycloalkyl, aryl, or heteroaryl; provided that when one of $R_1$, $R_2$, $R_3$, and $R_4$ is $NH_2$, at least another of $R_1$, $R_2$, $R_3$, and $R_4$ is not H or $R_5$ is not H; and when one of $R_1$ and $R_4$ is OH or $OCH_3$, the other of $R_1$ and $R_4$ is not H, one of $R_2$ and $R_3$ is not H, or $R_5$ is not H or $CH_3$.

In another aspect, this disclosure features a pharmaceutical composition that includes a compound of formula (I) described herein and a pharmaceutically acceptable carrier.

In another aspect, this disclosure features a method of treating cancer in a subject in need thereof. The method includes administering to the subject the pharmaceutical composition described herein in an amount effective to treat the cancer.

In still another aspect, this disclosure features a method of modulating (e.g., inhibiting) PRPK activity in a cell. The method includes contacting the cell in vitro with a compound of formula (I) described herein in an amount sufficient to modulate PRPK activity.

Also within the scope of this invention is a composition containing one or more of the compounds of formula (I) described herein for use in treating a cancer, and the use of such a composition for the manufacture of a medicament for the just-mentioned treatment.

The details of one or more embodiments are set forth in the description below. Other features, objects, and advantages will be apparent from the description, drawings, and claims.

DETAILED DESCRIPTION

This disclosure generally relates to compounds of formula (I) described herein, methods of synthesizing these compounds, and their uses (e.g., for treating a disease or modulating PRPK activity). In particular, this disclosure is based on the unexpected discovery that certain compounds (such as those of formula (I) described herein) can modulate (e.g., inhibit) the activities of PRPK in cancer cells and lead to cancer cell death.

PRPK Inhibitors

In some embodiments, this disclosure features PRPK inhibitors, such as the compounds of formula (I) or a salt thereof (e.g., a pharmaceutically acceptable salt thereof):

(I)

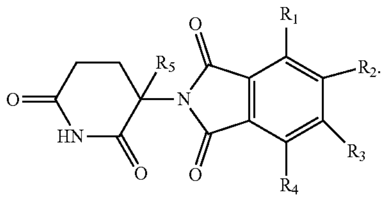

In formula (I), each of $R_1$, $R_2$, $R_3$, and $R_4$, independently, is H, halo, OR, COOR, C(O)R, C(O)N(RR'), NH—S(O)$_2$—R, N(RR'), $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_1$ and $R_2$, together with the carbon atoms to which they are attached, form a group comprising a five-membered or six-membered ring; or $R_2$ and $R_3$, together with the carbon atoms to which they are attached, form a group comprising a five-membered or six-membered ring; or $R_3$ and $R_4$, together with the carbon atoms to which they are attached, form a group comprising a five-membered or six-membered ring; $R_5$ is H or $C_1$-$C_{10}$ alkyl optionally substituted by aryl; each of $C_1$-$C_{10}$ arylalkyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, five-membered ring, and six-membered, independently, is optionally substituted by $C_1$-$C_{10}$ alkyl, halo, OR, or COOR; and each of R and R', independently, is H, $C_1$-$C_{10}$ alkyl, $C_3$-$C_{20}$ cycloalkyl, $C_3$-$C_{20}$ heterocycloalkyl, aryl, or heteroaryl; provided that when one of $R_1$, $R_2$, $R_3$, and $R_4$ is $NH_2$, at least another of $R_1$, $R_2$, $R_3$, and $R_4$ is not H or $R_5$ is not H; and when one of $R_1$ and $R_4$ is OH or $OCH_3$, the other of $R_1$ and $R_4$ is not H, or one of $R_2$ and $R_3$ is not H, or $R_5$ is not H or $CH_3$.

The term "alkyl" refers to a saturated, linear or branched hydrocarbon moiety, such as —$CH_3$ or —$CH(CH_3)_2$. As used herein, a "$C_1$-$C_{10}$ alkyl" can be a $C_1$-$C_4$ alkyl group, such as methyl, ethyl, n-propyl, isopropyl, n-butyl, i-butyl, or t-butyl.

The term "alkenyl" refers to a linear or branched hydrocarbon moiety that contains at least one carbon-carbon double bond, such as —CH═CH—$CH_3$. As used herein, a "$C_2$-$C_{10}$ alkenyl" can be a $C_2$-$C_4$ alkenyl group.

The term "alkynyl" refers to a linear or branched hydrocarbon moiety that contains at least one carbon-carbon triple bond, such as —C≡C—$CH_3$. As used herein, a "$C_2$-$C_{10}$ alkynyl" can be a $C_2$-$C_4$ alkynyl group.

The term "cycloalkyl" refers to a saturated, cyclic hydrocarbon moiety, such as cyclohexyl. As used herein, a "$C_3$-$C_{20}$ cycloalkyl" can be a $C_3$-$C_6$ cycloalkyl group.

The term "cycloalkenyl" refers to a non-aromatic, cyclic hydrocarbon moiety that contains at least one carbon-carbon double bond in the cyclic ring, such as cyclohexenyl. As used herein, a "$C_3$-$C_{20}$ cycloalkenyl" can be a $C_3$-$C_6$ cycloalkenyl group.

The term "heterocycloalkyl" refers to a saturated, cyclic moiety having at least one ring heteroatom (e.g., N, O, or S), such as 4-tetrahydropyranyl. In some embodiments, the heterocycloalkyl group mentioned herein can including one or more —C(O)— or a —C(S)— groups in which the carbon is a ring atom. As used herein, a "$C_1$-$C_{20}$ heterocycloalkyl" can be a $C_2$-$C_5$ heterocycloalkyl group.

The term "heterocycloalkenyl" refers to a non-aromatic, cyclic moiety having at least one ring heteroatom (e.g., N, O, or S) and at least one ring double bond (e.g., a carbon-carbon double bond, a double bond between a carbon atom or a heteroatom, or a double bond between two heteroatoms), such as pyranyl. In some embodiments, the heterocycloalkenyl group mentioned herein can including one or more —C(O)— or a —C(S)— groups in which the carbon is a ring atom. As used herein, a "$C_1$-$C_{20}$ heterocycloalkenyl" can be a $C_2$-$C_5$ heterocycloalkenyl group.

The term "aryl" refers to a hydrocarbon moiety having one or more aromatic rings. Examples of aryl moieties include phenyl (Ph), phenylene, naphthyl, naphthylene, pyrenyl, anthryl, and phenanthryl.

The term "heteroaryl" refers to a moiety having one or more aromatic rings that contain at least one heteroatom (e.g., N, O, or S). In some embodiments, the heteroaryl group mentioned herein can including a —C(O)— or a —C(S)— group in which the carbon is a ring atom. Examples of heteroaryl moieties include furyl, furylene, fluorenyl, pyrrolyl, thienyl, oxazolyl, imidazolyl, thiazolyl, pyridyl, pyrazolyl, pyrimidinyl, quinazolinyl, quinolyl, isoquinolyl, indolyl, pyridinonyl, imidazole-2-onyl, imidazole-2-thionyl, and pyrazine-2,3-dionyl.

The term "five-membered ring" or "six-membered ring" refers to an aromatic or non-aromatic, cyclic moiety having five or six ring atoms (in which one or more ring atoms can be a heteroatom such as N, O, or S). In some embodiments, the five-membered or six-membered ring mentioned herein can include one or more ring double bonds (e.g., a carbon-carbon double bond, a double bond between a carbon atom or a heteroatom, or a double bond between two heteroatoms). In some embodiments, the five-membered or six-membered ring mentioned herein can including one or more —C(O)— or a —C(S)— groups in which the carbon is a ring atom.

In some embodiments, alkyl, arylalkyl, alkenyl, alkynyl, cycloalkyl, cycloalkenyl, heterocycloalkyl, heterocycloalkenyl, aryl, phenylene, and heteroaryl mentioned herein can be optionally substituted. Possible substituents include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. Cycloalkyl, heterocycloalkyl, cycloalkenyl, heterocycloalkyl, aryl, and heteroaryl can also be fused with each other.

In some embodiments, each of $R_1$ and $R_4$, independently, is H, OR, NH—$S(O)_2$—R, N(RR'), or $C_1$-$C_{20}$ heterocycloalkenyl. For example, each of $R_1$ and $R_4$, independently, can be H, OH, $OCH_3$, NH—$S(O)_2$—$CH_3$, $NH_2$,

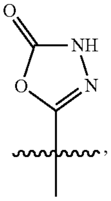
, or
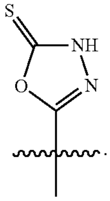
.

In some embodiments, each of $R_2$ and $R_3$, independently, is H, halo, OR, COOR, C(O)N(RR'), NH—$S(O)_2$—R, $C_1$-$C_{20}$ heterocycloalkenyl, or heteroaryl. For example, each of $R_2$ and $R_3$, independently, can be H, Br, OH, COOH, C(O)—(NH)—$CH_3$, $C(O)NH_2$, NH—$S(O)_2$—$CH_3$,

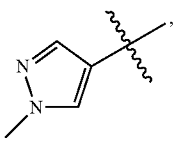
,
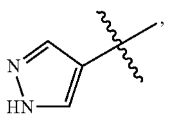
,
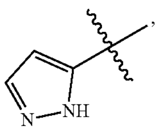
,
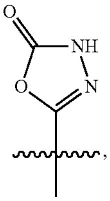
,
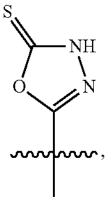
, or
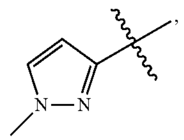

-continued

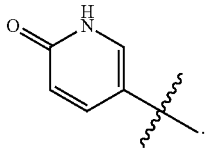

In some embodiments, $R_5$ is H or $C_1$-$C_{10}$ alkyl optionally substituted by aryl, in which the aryl is optionally substituted by COOR. For example, $R_5$ can be H, $CH_3$, $CH_2CH_3$, $CH(CH_3)_2$, $CH_2$-phenyl, or $CH_2$-(4-methoxycarbonylphenyl).

In some embodiments, $R_1$ and $R_2$, together with the carbon atoms to which they are attached, form a group comprising a five-membered or six-membered ring (e.g., a $C_3$-$C_5$ heterocycloalkyl, $C_3$-$C_5$ heterocycloalkenyl, or heteroaryl group). For example, $R_1$ and $R_2$, together with the carbon atoms to which they are attached, form

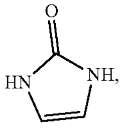, 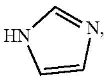, 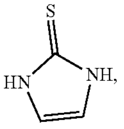,

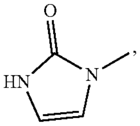, or 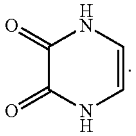.

In such embodiments, $R_3$ can be H or Br, $R_4$ can be H, and $R_5$ can be H or $CH_3$.

Exemplary compounds of formula (I) include Compounds 1-35 listed in Table 1 below.

TABLE 1

| Compound No. | Structure | Name |
|---|---|---|
| 1 | 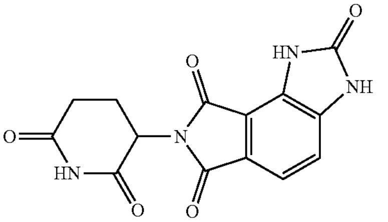 [SMILES: O=C1CCC(N2C(=O)c3ccc4[nH]c(=O)[nH]c4c3C2=O)C(=O)N1] | 2-(2,6-dioxopiperidin-3-yl)-5-(1H-pyrazol-4-yl)isoindoline-1,3-dione |
| 2 | 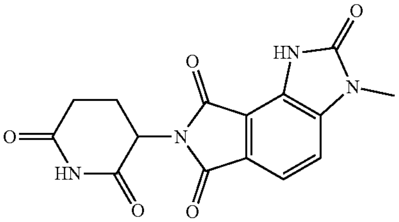 [SMILES: Cn1c(=O)[nH]c2c3c(ccc21)C(=O)N(C1CCC(=O)NC1=O)C3=O] | 7-(2,6-dioxopiperidin-3-yl)-3-methyl-1,3-dihydroimidazo[4,5-e]isoindole-2,6,8(7H)-trione |
| 3 | 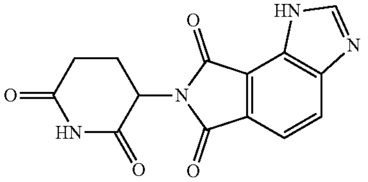 [SMILES: O=C1CCC(N2C(=O)c3ccc4nc[nH]c4c3C2=O)C(=O)N1] | 7-(2,6-dioxopiperidin-3-yl)imidazo [4,5-e]isoindole-6,8(1H,7H)-dione |
| 4 | 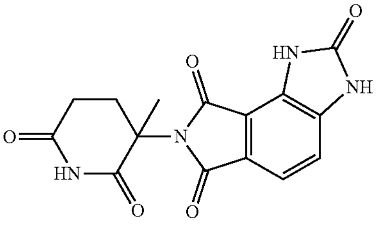 [SMILES: CC1(N2C(=O)c3ccc4[nH]c(=O)[nH]c4c3C2=O)CCC(=O)NC1=O] | 7-(3-methyl-2,6-dioxopiperidin-3-yl)-1,3-dihydroimidazo[4,5-e]isoindole-2,6,8(7H)-trione |

TABLE 1-continued

| Compound No. | Structure | Name |
|---|---|---|
| 5 | 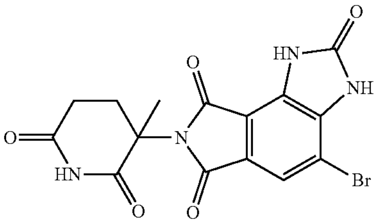 [SMILES: CC1(N2C(=O)c3cc(Br)c4[nH]c(=O)[nH]c4c3C2=O)CCC(=O)NC1=O] | 4-bromo-7-(3-methyl-2,6-dioxopiperidin-3-yl)-1,3-dihydroimidazo[4,5-e]isoindole-2,6,8(7H)-trione |
| 6 | 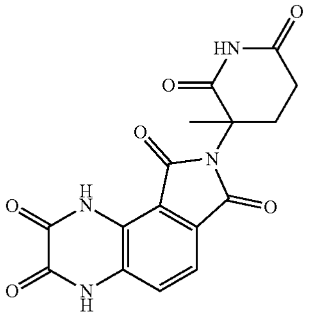 [SMILES: CC1(N2C(=O)c3ccc4[nH]c(=O)c(=O)[nH]c4c3C2=O)CCC(=O)NC1=O] | 8-(3-methyl-2,6-dioxopiperidin-3-yl)-1H-pyrrolo[3,4-f]quinoxaline-2,3,7,9(4H,8H)-tetraone |
| 7 | 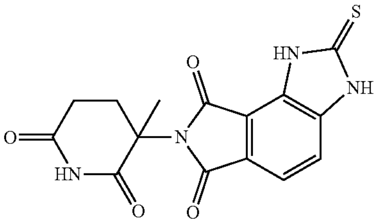 | 7-(3-methyl-2,6-dioxopiperidin-3-yl)-2-thioxo-2,3-dihydroimidazo[4,5-e]isoindole-6,8(1H,7H)-dione |
| 8 | 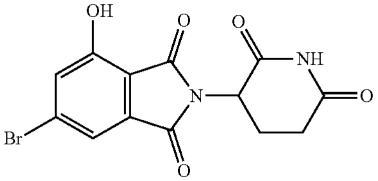 [SMILES: O=C1CCC(N2C(=O)c3cc(Br)cc(O)c3C2=O)C(=O)N1] | 6-bromo-2-(2,6-dioxopiperidin-3-yl)-4-hydroxyisoindoline-1,3-dione |
| 9 | 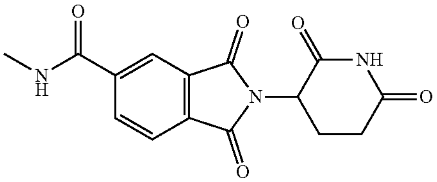 [SMILES: CNC(=O)c1ccc2c(c1)C(=O)N(C1CCC(=O)NC1=O)C2=O] | 2-(2,6-dioxopiperidin-3-yl)-N-methyl-1,3-dioxoisoindoline-5-carboxamide |
| 10 | 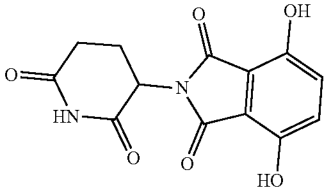 [SMILES: O=C1CCC(N2C(=O)c3c(O)ccc(O)c3C2=O)C(=O)N1] | 2-(2,6-dioxopiperidin-3-yl)-4,7-dihydroxyisoindoline-1,3-dione |
| 11 | 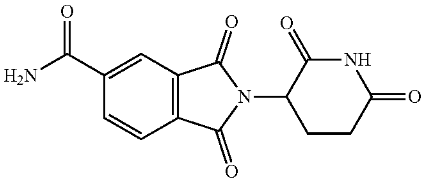 [SMILES: NC(=O)c1ccc2c(c1)C(=O)N(C1CCC(=O)NC1=O)C2=O] | 2-(2,6-dioxopiperidin-3-yl)-1,3-dioxoisoindoline-5-carboxamide |

TABLE 1-continued

| Compound No. | Structure | Name |
|---|---|---|
| 12 | 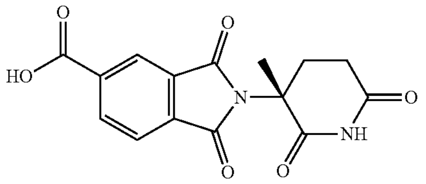 [SMILES: C[C@@]1(N2C(=O)c3ccc(C(=O)O)cc3C2=O)CCC(=O)NC1=O] | (R)-2-(3-methyl-2,6-dioxopiperidin-3-yl)-1,3-dioxoisoindoline-5-carboxylic acid |
| 13 | 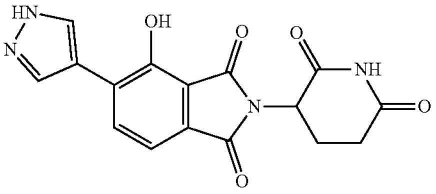 [SMILES: O=C1CCC(N2C(=O)c3ccc(-c4cn[nH]c4)c(O)c3C2=O)C(=O)N1] | 2-(2,6-dioxopiperidin-3-yl)-4-hydroxy-5-(1H-pyrazol-4-yl)isoindoline-1,3-dione |
| 14 | 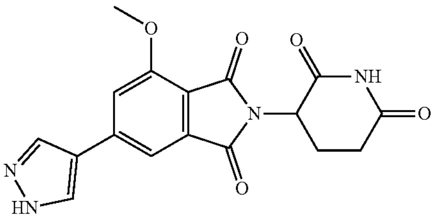 [SMILES: COc1cc(-c2cn[nH]c2)cc2c1C(=O)N(C1CCC(=O)NC1=O)C2=O] | 2-(2,6-dioxopiperidin-3-yl)-4-methoxy-6-(1H-pyrazol-4-yl)isoindoline-1,3-dione |
| 15 | 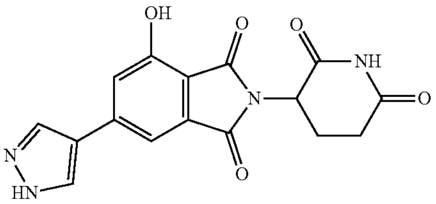 [SMILES: O=C1CCC(N2C(=O)c3cc(-c4cn[nH]c4)cc(O)c3C2=O)C(=O)N1] | 2-(2,6-dioxopiperidin-3-yl)-4-hydroxy-6-(1H-pyrazol-4-yl)isoindoline-1,3-dione |
| 16 | 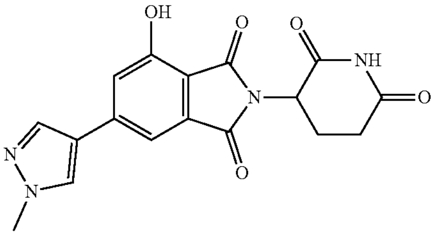 [SMILES: Cn1cc(-c2cc(O)c3c(c2)C(=O)N(C2CCC(=O)NC2=O)C3=O)cn1] | 2-(2,6-dioxopiperidin-3-yl)-4-hydroxy-6-(1-methyl-1H-pyrazol-4-yl)isoindoline-1,3-dione |
| 17 | 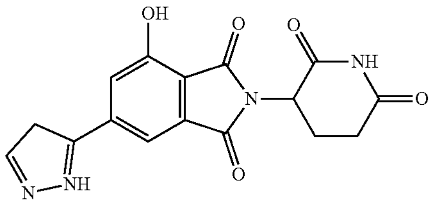 [SMILES: O=C1CCC(N2C(=O)c3cc(C4=NN=CC4)cc(O)c3C2=O)C(=O)N1] | 2-(2,6-dioxopiperidin-3-yl)-4-hydroxy-6-(1H-pyrazol-5-yl)isoindoline-1,3-dione |
| 18 | 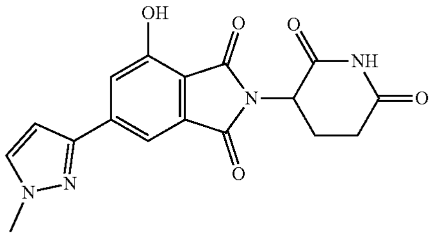 [SMILES: Cn1ccc(-c2cc(O)c3c(c2)C(=O)N(C2CCC(=O)NC2=O)C3=O)n1] | 2-(2,6-dioxopiperidin-3-yl)-4-hydroxy-6-(1-methyl-1H-pyrazol-3-yl)isoindoline-1,3-dione |

TABLE 1-continued

| Compound No. | Structure | Name |
| --- | --- | --- |
| 19 | 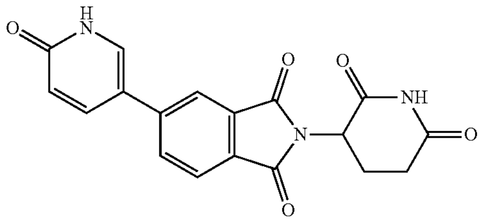 [SMILES: O=C1CCC(N2C(=O)c3ccc(-c4ccc(=O)[nH]c4)cc3C2=O)C(=O)N1] | 2-(2,6-dioxopiperidin-3-yl)-5-(6-oxo-1,6-dihydropyridin-3-yl)isoindoline-1,3-dione |
| 20 | 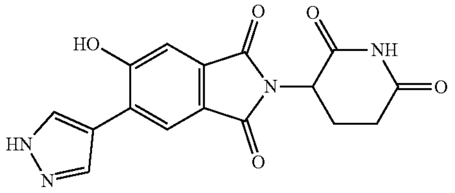 [SMILES: O=C1CCC(N2C(=O)c3cc(O)c(-c4cn[nH]c4)cc3C2=O)C(=O)N1] | 2-(2,6-dioxopiperidin-3-yl)-5-hydroxy-6-(1H-pyrazol-4-yl)isoindoline-1,3-dione |
| 21 | 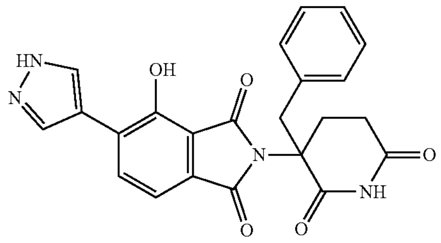 [SMILES: O=C1CCC(Cc2ccccc2)(N2C(=O)c3ccc(-c4cn[nH]c4)c(O)c3C2=O)C(=O)N1] | 2-(3-benzyl-2,6-dioxopiperidin-3-yl)-4-hydroxy-5-(1H-pyrazol-4-yl)isoindoline-1,3-dione |
| 22 | 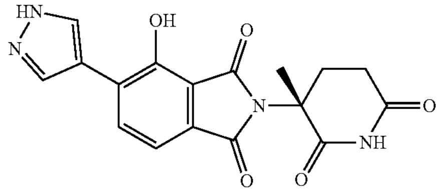 [SMILES: C[C@@]1(N2C(=O)c3ccc(-c4cn[nH]c4)c(O)c3C2=O)CCC(=O)NC1=O] | (R)-4-hydroxy-2-(3-methyl-2,6-dioxopiperidin-3-yl)-5-(1H-pyrazol-4-yl)isoindoline-1,3-dione |
| 23 | 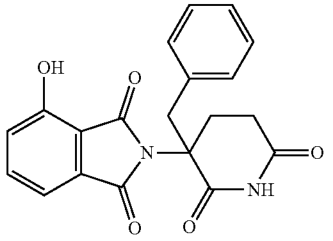 [SMILES: O=C1CCC(Cc2ccccc2)(N2C(=O)c3cccc(O)c3C2=O)C(=O)N1] | 2-(3-benzyl-2,6-dioxopiperidin-3-yl)-4-hydroxyisoindoline-1,3-dione |
| 24 | 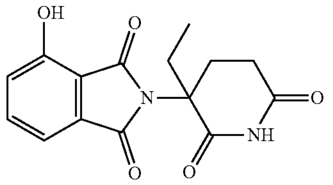 [SMILES: CCC1(N2C(=O)c3cccc(O)c3C2=O)CCC(=O)NC1=O] | 2-(3-ethyl-2,6-dioxopiperidin-3-yl)-4-hydroxyisoindoline-1,3-dione |
| 25 | 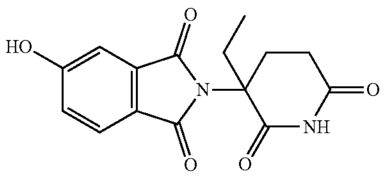 [SMILES: CCC1(N2C(=O)c3ccc(O)cc3C2=O)CCC(=O)NC1=O] | 2-(3-ethyl-2,6-dioxopiperidin-3-yl)-5-hydroxyisoindoline-1,3-dione |

TABLE 1-continued

| Compound No. | Structure | Name |
|---|---|---|
| 26 | 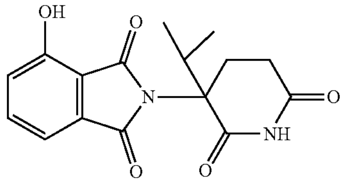 [SMILES: CC(C)C1(N2C(=O)c3cccc(O)c3C2=O)CCC(=O)NC1=O] | 4-hydroxy-2-(3-isopropyl-2,6-dioxopiperidin-3-yl)isoindoline-1,3-dione |
| 27 | 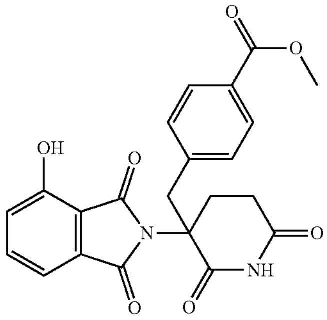 [SMILES: COC(=O)c1ccc(CC2(N3C(=O)c4cccc(O)c4C3=O)CCC(=O)NC2=O)cc1] | methyl 4-((3-(4-hydroxy-1,3-dioxoisoindolin-2-yl)-2,6-dioxopiperidin-3-yl)methyl)benzoate |
| 28 | 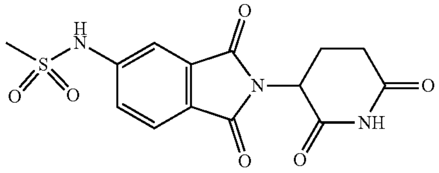 [SMILES: CS(=O)(=O)Nc1ccc2c(c1)C(=O)N(C1CCC(=O)NC1=O)C2=O] | N-(2-(2,6-dioxopiperidin-3-yl)-1,3-dioxoisoindolin-5-yl)methanesulfonamide |
| 29 | 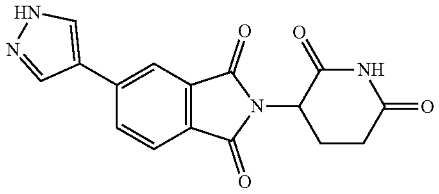 [SMILES: O=C1CCC(N2C(=O)c3ccc(-c4cn[nH]c4)cc3C2=O)C(=O)N1] | 2-(2,6-dioxopiperidin-3-yl)-5-(1H-pyrazol-4-yl)isoindoline-1,3-dione |
| 30 | 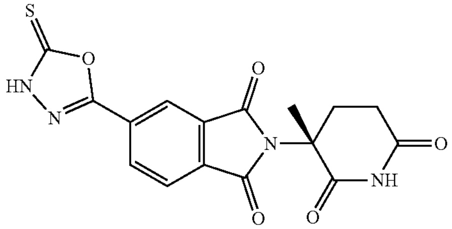 [SMILES: C[C@@]1(N2C(=O)c3ccc(-c4n[nH]c(=S)o4)cc3C2=O)CCC(=O)NC1=O] | (R)-2-(3-methyl-2,6-dioxopiperidin-3-yl)-5-(5-thioxo-4,5-dihydro-1,3,4-oxadiazol-2-yl) isoindoline-1,3-dione |
| 31 | 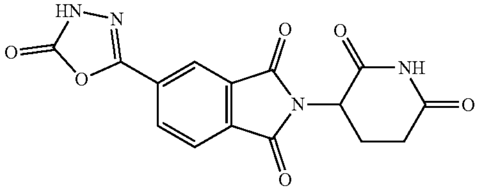 [SMILES: O=C1CCC(N2C(=O)c3ccc(-c4n[nH]c(=O)o4)cc3C2=O)C(=O)N1] | 2-(2,6-dioxopiperidin-3-yl)-5-(5-oxo-4,5-dihydro-1,3,4-oxadiazol-2-yl)isoindoline-1,3-dione |

TABLE 1-continued

| Compound No. | Structure | Name |
| --- | --- | --- |
| 32 | 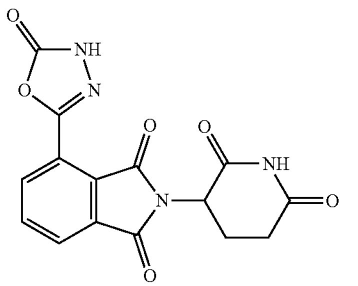 [SMILES: O=C1CCC(N2C(=O)c3cccc(-c4n[nH]c(=O)o4)c3C2=O)C(=O)N1] | 2-(2,6-dioxopiperidin-3-yl)-4-(5-oxo-4,5-dihydro-1,3,4-oxadiazol-2-yl)isoindoline-1,3-dione |
| 33 | 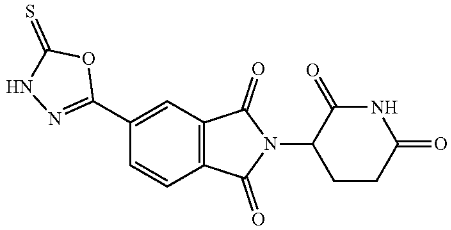 [SMILES: O=C1CCC(N2C(=O)c3ccc(-c4n[nH]c(=S)o4)cc3C2=O)C(=O)N1] | 2-(2,6-dioxopiperidin-3-yl)-5-(5-thioxo-4,5-dihydro-1,3,4-oxadiazol-2-ylisoindoline-1,3-dione |
| 34 | 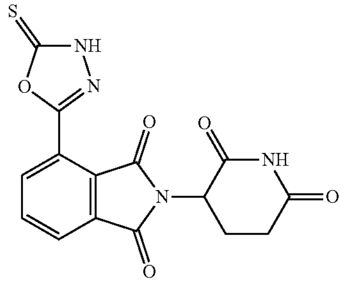 [SMILES: O=C1CCC(N2C(=O)c3cccc(-c4n[nH]c(=S)o4)c3C2=O)C(=O)N1] | 2-(2,6-dioxopiperidin-3-yl)-4-(5-thioxo-4,5-dihydro-1,3,4-oxadiazol-2-yl)isoindoline-1,3-dione |
| 35 | 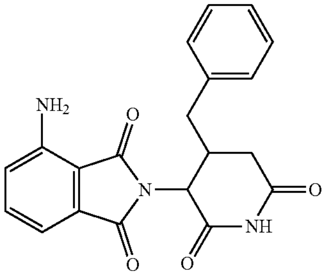 [SMILES: Nc1cccc2c1C(=O)N(C1C(=O)NC(=O)CC1Cc1ccccc1)C2=O] | 4-amino-2-(3-benzyl-2,6-dioxopiperidin-3-yl)isoindoline-1,3-dione |

The compounds of formula (I) described herein can contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The compounds described herein include the compounds themselves, as well as their salts, prodrugs, and solvates (e.g., pharmaceutically acceptable salts, prodrugs and solvates), if applicable. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water (which forms a hydrate), ethanol, isopropanol, ethyl acetate, acetic acid, and ethanolamine.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The present disclosure also includes pharmaceutically acceptable salts of the compounds of formula (I) described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, inorganic or organic acid salts of basic residues such as amines; alkali or organic salts of acidic residues such as carboxylic acids; and the like. Specific examples of pharmaceutically acceptable salts include acid addition salts, e.g., salts formed by reaction between a compound of formula (I) and hydrohalogen acids (such as hydrochloric acid or hydrobromic acid), mineral acids (such as sulfuric acid, phosphoric acid and nitric acid), and aliphatic, alicyclic, aromatic or heterocyclic sulfonic or carboxylic acids (such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid, and naphthalenesulphonic acid). Lists of other suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described in the present application can also include all isotopes of atoms occurring in the intermediates or final compounds. Isotopes include those atoms having the same atomic number but different mass numbers. For example, isotopes of hydrogen include tritium and deuterium.

Synthesis

The compounds of formula (I) described in this disclosure, including salts thereof, can be prepared using known organic synthesis techniques and can be synthesized according to any of numerous possible synthetic routes. Examples 1-35 below provide detailed descriptions of how compounds 1-35 were actually prepared.

Scheme I shown below illustrates a typical synthetic route for synthesizing exemplary compounds 1-35 described herein.

Scheme I

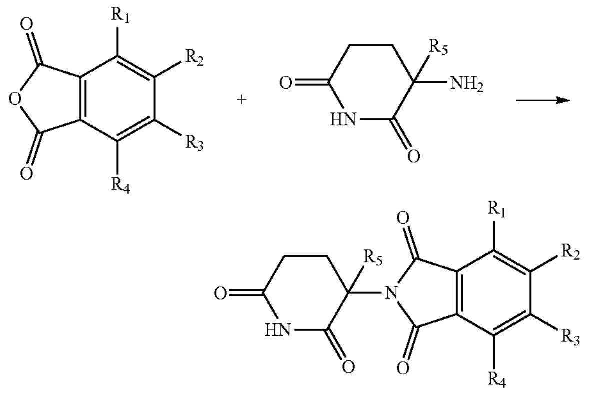

In Scheme I, $R_1$, $R_2$, $R_3$, $R_4$, and $R_5$ can be those defined above. As shown in Scheme I, a compound of formula (I) can be synthesized by reacting a substituted phthalic anhydride compound with a substituted or unsubstituted 3-aminopiperidine-2,6-dione compound through an amidation reaction. The compounds of formula (I) can be prepared in methods that include reaction steps either before or after the above reaction. For example, $R_1$, $R_2$, $R_3$, $R_4$, and $R_5$ in the compound of formula (I) can be formed either before the above reaction or after the above reaction (e.g., upon further modifications). The synthesized compounds can then be purified by a suitable method such as column chromatography, high-pressure liquid chromatography, or recrystallization.

The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric or excess amount of the appropriate base or acid in water or in an organic solvent, or in a mixture of the two. In some embodiments, the salts can be formed in non-aqueous media such as ether, ethyl acetate, alcohols (e.g., methanol, ethanol, isopropanol, or butanol) or acetonitrile (ACN).

The reactions for preparing compounds of the present disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of two or more solvents. Depending on the particular reaction step, suitable solvents can be selected by the skilled artisan.

Preparation of compounds described in the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G M. Wuts, *Protective Groups in Organic Synthesis,* 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present application. Cis and trans geometric isomers of the compounds of the present application can be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds described in the present disclosure, or salts thereof, are substantially isolated. The term "substantially isolated" is meant that the compound is at least partially or substantially separated from the environment in which it was formed or detected. Partial separation can include, for example, a composition enriched in the compounds described in the present disclosure. Substantial separation can include compositions containing at least about 50%, at least about 60%, at least about 70%, at least about 80%, at least about 90%, at least about 95%, at least about 97%, or at least about 99% by weight of the compounds described in the present disclosure, or salt thereof. Methods for isolating compounds and their salts are routine in the art.

Evaluation Methods

In some embodiments, this disclosure features an in vitro methods that can be used to evaluate the compounds of formula (I) described herein for their efficacy in modulating PRPK activity in an assay. The method can include contacting the PRPK enzyme in vitro with a compound of formula (I) described herein in an amount sufficient to modulate PRPK activity.

The compounds of formula (I) described herein can also be evaluated by a screening method, such as an assay that identifies compounds that inhibit the proliferation of cancer cells. Alternatively or in addition, compounds can be evaluated by using an assay that identifies compounds that inhibit the activation of the downstream targets of PRPK, such as ribonucleotide reductase-1, telomerase reverse transcriptase, and cyclin-dependent kinase inhibitor 2C.

For example, the screening method can include exposing a multiple myeloma (MM) cell line (e.g., MM.1S and H929 cell lines) to various doses of a compound of formula (I) for various time periods. A candidate compound that inhibits cell survival can be identified based on the ability of the cell to proliferate in the presence of the compound. Such a screening method can be carried out in a container that includes the cells from a specific cell line, liquid media, and a candidate compound. The container can be, for example, a petri dish, a tissue culture flask, 24-well plate, a 48-well plate, a 96-well plate, a 384-well plate, a 1536-well plate, a 3456-well plate, or any other suitable container. In a high throughput screening method, each well of the container can contain a different candidate compound. As would be appreciated in the art, the screening method can be automated to obtain high throughput. For example, an MTS assay can be performed in liquid medium in standard microtiter plates. In addition, because manual screening of the plates can be slow, labor intensive and subjective, an automated staining method can be used in a high throughput screening method to distinguish live from dead cells.

The compounds of formula (I) described herein can induce inhibition of cell proliferation. Induction of the inhibition of proliferation can mean inducing or enhancing the suppression of proliferation signals in a cell (e.g., a cancer cell). For example, induction of the inhibition of proliferation can mean inducing or enhancing cell death in a cell. As another example, induction of the inhibition of proliferation can mean inducing or enhancing apoptosis in a cell. As another example, induction of the inhibition of proliferation can mean inducing or enhancing the state of quiescence in a cell. As yet another example, induction of the inhibition of proliferation can mean inducing or enhancing autophagy. Accordingly, the compounds of formula (I) described herein can be used in methods of inducing the suppression of proliferation in a cell. The methods can include contacting a cell with a compound, salt, or composition described herein, in an amount effective to induce suppression of proliferation in the cell. The contacting can be done in vivo or in vitro.

Methods of Treatment

This disclosure also features a method for treating a PRPK mediated disorder. The method includes administering to a subject (e.g., a patient diagnosed as suffering from or at risk for a PRPK mediated disorder) in need thereof an effective amount of one or more of the compounds of formula (I) described herein or a pharmaceutical composition containing one or more of the compounds of formula (I) described herein. Examples of PRPK mediated disorders include cellular proliferative and/or differentiative disorders (such as cancers). The method can optionally include a step of identifying (e.g., diagnosing) the patient as suffering from or at risk for a PRPK mediated disorder.

The term "treating" or "treatment" refers to administering one or more of the compounds of formula (I) or their compositions described herein to a subject who has an a disorder treatable with such compounds or compositions, and/or a symptom of such a disorder, and/or a predisposition toward such a disorder, with the purpose to confer a therapeutic effect, e.g., to cure, relieve, alter, affect, ameliorate, or prevent the above-described disorder, the symptom of it, or the predisposition toward it.

The term "subject" or "patient" is used throughout the disclosure to describe an animal, human or non-human, to whom treatment according to the methods described herein is provided. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

"An effective amount" or "an amount effective" refers to the amount of an active compound that is required to confer a therapeutic effect on the treated patient. Effective doses will vary, as recognized by those skilled in the art, depending on the types of diseases treated, route of administration, excipient usage, and the possibility of co-usage with other therapeutic treatment.

Examples of cellular proliferative and/or differentiative disorders include cancer, such as carcinoma, sarcoma, metastatic disorders and hematopoietic neoplastic disorders. Specific examples of cancers include multiple myeloma, cervical cancer, colon cancer, and skin cancer.

The term "cancer" refers to cells having the capacity for autonomous growth. Examples of such cells include cells having an abnormal state or condition characterized by rapidly proliferating cell growth. The term is meant to include cancerous growths, e.g., tumors (e.g., solid tumors); oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

A metastatic tumor can arise from a multitude of primary tumor types, including but not limited to, those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

Cancers that can be treated using the methods and compositions of the present disclosure include, for example, cancers of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; Hodgkins disease, non-Hodgkins leukemia, bone marrow, sarcomas, choriocarcinoma, and lymphoma, among others.

Individuals considered at risk for developing cancer can benefit particularly from the invention, primarily because prophylactic treatment can begin before there is any evidence of the disorder. Individuals "at risk" include, e.g., individuals exposed to carcinogens (e.g., by consumption such as by inhalation and/or ingestion) at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue)) can benefit from such prophylactic treatment.

Other examples of cellular proliferative and/or differentiative disorders that can be treated by the compounds described herein include inflammatory diseases and bone resorption disorders. Examples of inflammatory disorders include neurodegenerative disease, multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, Type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, viral infections, bacterial infections, organ transplant conditions, skin transplant conditions, graft rejection (including allograft rejection and graft-versus-host disease), spondyloarthropathies, scleroderma, vasculitis, and psoriasis (including T-cell mediated psoriasis). Other inflammatory disorders have been described in, e.g., U.S. Application Publication No. 20020155166, the entire contents of which are herein incorporated by reference.

In some embodiments, this disclosure features a method of treating a condition associated with unwanted angiogenesis. The method includes administering to a patient diagnosed as suffering from or at risk for a condition associated with unwanted angiogenesis an effective amount of one or more of the compounds formula (I) described herein or a pharmaceutical composition thereof, wherein the condition associated with unwanted angiogenesis is not cancer. The method can optionally include a step of identifying (e.g., diagnosing) the patient as suffering from or at risk for a condition associated with unwanted angiogenesis. In an embodiment, the condition is rheumatoid arthritis, lupus, psoriasis, diabetic retinopathy, retinopathy of prematurity, macular degeneration, corneal graft rejection, neovascular glaucoma, retrolental fibroplasia, rubeosis, Osler-Weber Syndrome, myocardial angiogenesis, plaque neovascularization, telangiectasia, or angiofibroma, or any combination thereof.

Skilled practitioners will appreciate that a patient can be diagnosed by a physician (or veterinarian, as appropriate for the patient being diagnosed) as suffering from or at risk for a condition described herein (e.g., cancer) by any method known in the art, such as by assessing a patient's medical history, performing diagnostic tests, and/or by employing imaging techniques.

Skilled practitioners will also appreciate that the compounds or their compositions described herein need not be administered to a patient by the same individual who diagnosed the patient (or prescribed the composition for the patient). The compounds or their compositions can be administered (and/or administration can be supervised), e.g., by the diagnosing and/or prescribing individual, and/or any other individual, including the patient her/himself (e.g., where the patient is capable of self-administration).

A compound of formula (I) or its composition effective to treat a disorder described herein (e.g., cancer) can be administered to (or prescribed for) a patient, e.g., by a physician or veterinarian, on or after the day the patient is diagnosed as suffering any of these disorders or conditions, or as having any risk factor associated with an increased likelihood that the patient will develop such disorder(s) or condition(s) (e.g., the patient has recently been, is being, or will be exposed to a carcinogen(s)). The compound of formula (I) or its composition can be administered to the patient intermittently or continuously. For example, the compound of formula (I) or its composition can be administered for at least about 1, 2, 4, 6, 8, 10, 12, 14, 18, or 20 days, or greater than 20 days (e.g., 1, 2, 3, 5, or 6 months) or until the patient no longer exhibits symptoms of the condition or disorder, or until the patient is diagnosed as no longer being at risk for the condition or disorder. In a given day, a compound of formula (I) or its composition can be administered continuously for the entire day, or intermittently or for up to 23 hours per day, e.g., up to 20, 15, 12, 10, 6, 3, or 2 hours per day, or up to 1 hour per day.

If the patient needs to be treated with chemotherapy, radiation therapy, immunotherapy, gene therapy, and/or surgery (e.g., because prescribed by a physician or veterinarian), the patient can be treated with a compound of formula (I) or its composition described herein before, during, and/or after administration of the chemotherapy, radiation therapy, and/or surgery. For example, with regard to chemotherapy, immunotherapy, gene therapy, and radiation therapy, a compound of formula (I) or its composition can be administered to the patient, intermittently or continuously, starting 0 to 20 days before the chemotherapy, immunotherapy, gene therapy, or radiation therapy is administered (and where multiple doses are given, before each individual dose), e.g., starting at least about 30 minutes (e.g., about 1, 2, 3, 5, 7, or 10 hours, or about 1, 2, 4, 6, 8, 10, 12, 14, 18, or 20 days, or greater than 20 days) before the administration. Alternatively or in addition, the compound of formula (I) or its composition can be administered to the patient concurrent with administration of chemotherapy, immunotherapy, gene therapy, or radiation therapy. Alternatively or in addition, the compound of formula (I) or its composition can be administered to the patient after administration of chemotherapy, immunotherapy, gene therapy, or radiation therapy, e.g., starting immediately after administration, and continuing intermittently or continuously for about 1, 2, 3, 5, 7, or 10 hours, or about 1, 2, 5, 8, 10, 20, 30, 50, or 60 days, one year, indefinitely, or until a physician determines that administration of the composition is no longer necessary. With regard to surgical procedures, the compound of formula (I) or its composition can be administered systemically or locally to a patient prior to, during, and/or after a surgical procedure is performed. The compound of formula (I) or its composition can be administered to the patient intermittently or continuously, for 1 hour, 2, hours, 3 hours, 4 hours, 6, hours, 12 hours, or about 1, 2, 4, 6, 8, 10, 12, 14, 18, or 20 days, or greater than 20 days, before the procedure. It can be administered in the time period immediately prior to the surgery and optionally continue through the procedure, or the administration can cease at least 15 minutes before the surgery begins (e.g., at least 30 minutes, 1 hour, 2 hours 3 hours, 6 hours, or 24 hours before the surgery begins). Alternatively or in addition, the compound of formula (I) or its composition can be administered to the patient during the procedure. Alternatively or in addition, the compound of formula (I) or its composition can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, 1 year, indefinitely, or until the patient no longer suffers from, or is at risk for, cancer after the completion of the procedure.

Combination Therapy

In some embodiments, a compound described in the present disclosure, or a pharmaceutically acceptable salt thereof, can be used in combination with another therapeutic agent to treat diseases such as cancer. For example, the additional agent can be a therapeutic agent that is art-recognized as being useful to treat the disease or condition being treated by the compound described herein. In some embodiments, the additional agent can be an anti-cancer drug, such as Dexamethasone, Vincristine, or a PAK inhibitor (e.g., PF-3758309 described in Murray et al., PNAS, Vol. 107, No. 20, 9446-9451 (2010)). The additional agent also can be an agent that imparts a beneficial attribute to the therapeutic composition (e.g., an agent that affects the viscosity of the composition).

The combination therapy contemplated by this disclosure includes, for example, administration of one or more compounds of formula (I) described herein, or a pharmaceutically acceptable salt thereof, and additional agent(s) in a single pharmaceutical formulation or in separate pharmaceutical formulations. Alternatively or in addition, combination therapy can include administering at least two compounds described herein, or pharmaceutically acceptable salts thereof, in the same or separate pharmaceutical formulations. In other words, co-administration shall mean the administration of at least two agents to a subject so as to provide the beneficial effects of the combination of both agents. For example, the agents can be administered simultaneously or sequentially over a period of time.

In some embodiments, the methods described herein can be used in combination with the therapies and combination therapies recited above.

Pharmaceutical Formulations and Dosage Forms

When employed as pharmaceuticals, the compounds of formula (I) described herein can be administered in the form of pharmaceutical compositions. The pharmaceutical compositions described in the present disclosure can include at least one (e.g., at least 2, 3, 4, 5, or at least 6) compound(s) depicted in formula (I), (e.g., compounds 1-35), or a pharmaceutically acceptable salt thereof, and a pharmaceutically acceptable carrier.

These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the treatment method described herein, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Typical doses can range from about 0.01 μg/kg to about 50 mg/kg (e.g., from about 0.1 μg/kg to about 25 mg/kg, from about 1 μg/kg to about 10 mg/kg, from about 10 μg/kg to about 5 mg/kg, or from about 0.1 mg/kg to about 1 mg/kg) of body weight per day. In some embodiments, suitable daily doses can range from about 10 μg/kg to about 100 μg/kg of body weight.

To practice the method described in the present disclosure, one or more compounds of formula (I) described herein and their compositions can be administered parenterally, orally, nasally, rectally, topically, and/or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in buffered saline or 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as TWEENs or SPANs or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds described above can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds described herein can also be prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of formulating suitable for pharmaceutical compositions are known in the art. See, e.g., the books in the series *Drugs and the Pharmaceutical Sciences: a Series of Textbooks and Monographs* (Dekker, N.Y.).

The compounds described herein can be preliminarily screened for their efficacy in treating above-described diseases by the screening method described herein and then confirmed by additional animal experiments and/or clinic trials. Other screening methods will also be apparent to those of ordinary skill in the art.

Kits

The present application also includes pharmaceutical kits useful, for example, in the treatment or prevention of a PRPK mediated disorder (e.g. cancer), which include one or more containers containing a pharmaceutical composition comprising a therapeutically effective amount of a compound of formula (I) described herein. Such kits can further include, if desired, one or more of various conventional pharmaceutical kit components, such as, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The contents of all publications cited herein (e.g., patents, patent application publications, and articles) are hereby incorporated by reference in their entirety.

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1: Synthesis of 2-(2,6-dioxopiperidin-3-yl)-5-(1H-pyrazol-4-yl)isoindoline-1,3-dione (Compound 1)

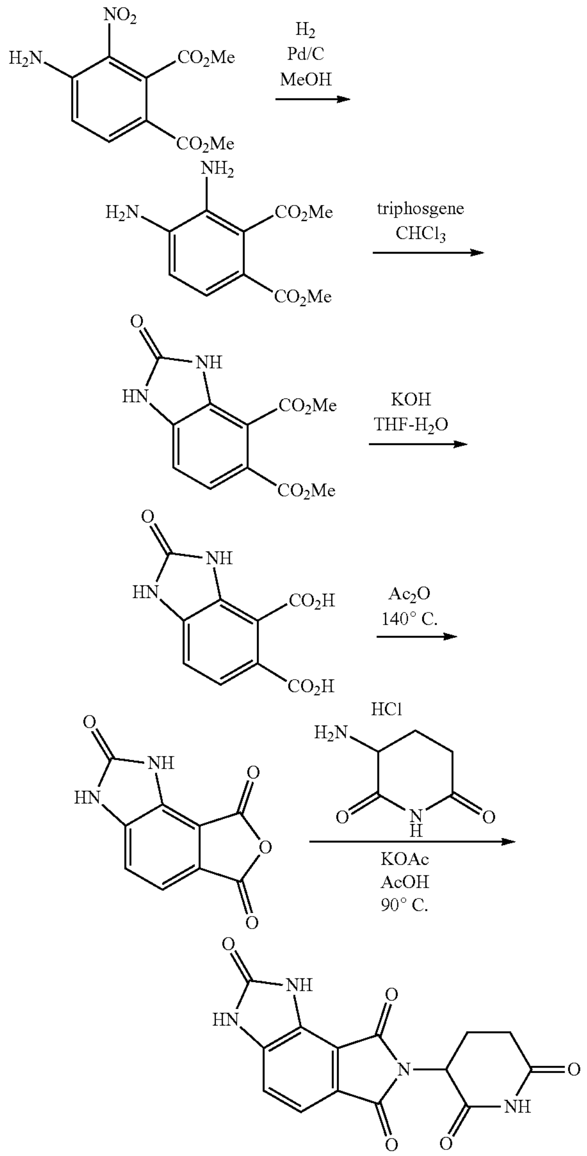

Synthesis of dimethyl 2-oxo-2,3-dihydro-1H-benzo[d]imidazole-4,5-dicarboxylate

The suspension mixture of dimethyl 4-amino-3-nitrophthalates (200 mg, 0.79 mmol) and palladium on carbon (10%, 180 mg) in MeOH (10 mL) under $H_2$ atmosphere was stirred at room temperature for 16 hours. The reaction mixture was filtered through a Celite pad that was washed with MeOH. The filtrated was concentrated under reduced pressure to give crude dimethyl 3,4-diaminophthalate as a dark brown gum. To the stirred solution of dimethyl 3,4-diaminophthalate in $CHCl_3$ (3 mL) was added triphosgene (58 mg, 0.40 mmol) at room temperature. After being stirred at 40° C. for 16 hours, water was added. The reaction mixture was extracted with $CHCl_3$ and the organic extract was concentrated under reduced pressure to give dimethyl 2-oxo-2,3-dihydro-1H-benzo[d]imidazole-4,5-dicarboxylate as a brown viscous solid.

$^1$H NMR (500 MHz, DMSO-$d_6$) δ 11.24 (s, 1H), 11.13 (s, 1H), 7.43 (d, J=8.1 Hz, 1H), 7.11 (dd, J=8.1, 0.8 Hz, 1H), 3.85 (s, 3H), 3.77 (s, 3H).

Synthesis of 2-oxo-2,3-dihydro-1H-benzo[d]imidazole-4,5-dicarboxylic acid

The suspension mixture of dimethyl 2-oxo-2,3-dihydro-1H-benzo[d]imidazole-4,5-dicarboxylate (67.7 mg, 0.27 mmol) and 2M KOH (675 μL, 1.35 mmol) in THF (1 mL) and MeOH (0.5 mL) was stirred at 50° C. for 5 hours. After cooling, HCl was carefully added to acidify the medium. After being stirred at room temperature for 16 hours, the precipitate was collected by filtration then washed with water to give 2-oxo-2,3-dihydro-1H-benzo[d]imidazole-4,5-dicarboxylic acid as a brown solid. 16.7 mg (28%)

$^1$H NMR (500 MHz, DMSO-$d_6$) δ 10.99 (s, 1H), 10.19 (s, 1H), 7.97 (d, J=8.2 Hz, 1H), 7.05 (d, J=8.2 Hz, 1H).

Synthesis of 2-(2,6-dioxopiperidin-3-yl)-5-(1H-pyrazol-4-yl)isoindoline-1,3-dione (Compound 1)

The suspension of 2-oxo-2,3-dihydro-1H-benzo[d]imidazole-4,5-dicarboxylic acid (8.6 mg, 0.039 mmol) in $Ac_2O$ (100 μL) was stirred at 140° C. for 5 hours and then concentrated in vacuo. To the residue was added 3-aminopiperidine-2,6-dione hydrochloride (19.1 mg, 0.12 mmol), KOAc (11.4 mg, 0.12 mmol) and AcOH (0.2 mL). After being stirred at 90° C. for 16 hours, the residue was directly purified by reverse phase preparative HPLC to give the title compound (5.0 mg, 41% in 2 steps) as a gray solid.

$^1$H NMR (500 MHz, DMSO-$d_6$) δ 11.90 (s, 1H), 11.49 (s, 1H), 11.11 (s, 1H), 7.49 (d, J=7.8 Hz, 1H), 7.29-7.23 (m, 1H), 5.10 (dd, J=12.8, 5.3 Hz, 1H), 2.90 (ddd, J=16.9, 13.8, 5.3 Hz, 1H), 2.64-2.52 (m, 2H), 2.05 (m, 1H). LC/MS RT 0.38 min, m/z 313.2 $[M-H]^-$.

Example 2: Synthesis of 7-(2,6-dioxopiperidin-3-yl)-3-methyl-1,3-dihydroimidazo[4,5-e]isoindole-2,6,8(7H)-trione (Compound 2)

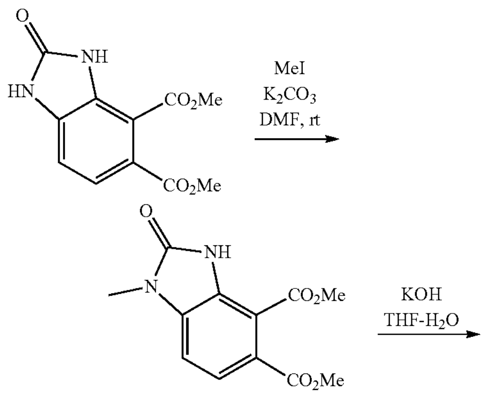

-continued

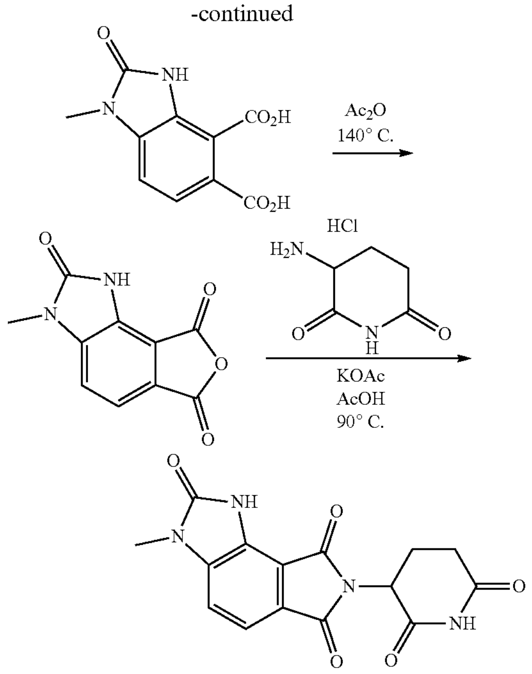

To the stirred suspension of dimethyl 2-oxo-2,3-dihydro-1H-benzo[d]imidazole-4,5-dicarboxylate (20 mg, 0.080 mmol) prepared in Example 1 and $K_2CO_3$ (16.5 mg, 0.12 mmol) in DMF (0.3 mL) was added iodomethane (5.0 μL, 0.080 mmol) at room temperature. After being stirred at room temperature for 16 hours, the reaction mixture was directly purified by reverse phase preparative HPLC to give dimethyl 1-methyl-2-oxo-2,3-dihydro-1H-benzo[d]imidazole-4,5-dicarboxylate as a mixture with dimethylated product, and the mixture was used for further conversion without additional purification. 7-(2,6-dioxopiperidin-3-yl)-3-methyl-1,3-dihydroimidazo[4,5-e]isoindole-2,6,8(7H)-trione was synthesized by the same procedure as Example 1 by using the crude dimethyl 1-methyl-2-oxo-2,3-dihydro-1H-benzo[d]imidazole-4,5-dicarboxylate instead of dimethyl 2-oxo-2,3-dihydro-1H-benzo[d]imidazole-4,5-dicarboxylate.

$^1$H NMR (500 MHz, DMSO-$d_6$) δ 11.78 (s, 1H), 11.11 (s, 1H), 7.53 (d, J=7.8 Hz, 1H), 7.32 (d, J=7.8 Hz, 1H), 5.17-5.10 (m, 1H), 3.70 (s, 3H), 2.90 (ddd, J=17.7, 14.0, 5.5 Hz, 1H), 2.64-2.52 (m, 2H), 2.11-1.98 (m, 1H). LC/MS RT 0.49 min, m/z 327.3 [M−H]$^-$.

Example 3: Synthesis of 7-(2,6-dioxopiperidin-3-yl)imidazo[4,5-e]isoindole-6,8(1H,7H)-dione (Compound 3)

A suspension of dimethyl 3,4-diaminophthalate (82 mg, 0.37 mmol) in ethyl orthoformate (1 mL) was stirred at 150° C. for 2 hours and then the mixture was purified by silica gel column chromatography (1 to 15% MeOH in DCM) to give crude dimethyl 1H-benzo[d]imidazole-6,7-dicarboxylate as a pale brown solid (82 mg). 7-(2,6-dioxopiperidin-3-yl)imidazo[4,5-e]isoindole-6,8(1H,7H)-dione was synthesized by the same procedure as Example 1 by using dimethyl 1H-benzo[d]imidazole-6,7-dicarboxylate instead of dimethyl 2-oxo-2,3-dihydro-1H-benzo[d]imidazole-4,5-dicarboxylate.

$^1$H NMR (500 MHz, DMSO-$d_6$) δ 11.13 (s, 1H), 8.67 (s, 1H), 8.07 (d, J=8.1 Hz, 1H), 7.73 (d, J=8.1 Hz, 1H), 5.16 (dd, J=12.7, 5.4 Hz, 1H), 2.93 (ddd, J=17.6, 14.0, 5.3 Hz, 1H), 2.67-2.56 (m, 2H), 2.14-2.05 (m, 2H). LC/MS RT 0.39 min, m/z 299.4 [M+H]$^+$.

Example 4: Synthesis of 7-(3-methyl-2,6-dioxopiperidin-3-yl)-1,3-dihydroimidazo[4,5-e]isoindole-2,6,8(7H)-trione (Compound 4)

7-(3-methyl-2,6-dioxopiperidin-3-dihydroimidazo[4,5-e]isoindole-2,6,8(7H)-trione was synthesized by the same procedure as Example 1 by using 3-amino-3-methylpiperidine-2,6-dione hydrochloride instead of 3-aminopiperidine-2,6-dione hydrochloride.

$^1$H NMR (500 MHz, DMSO-$d_6$) δ 11.83 (s, 1H), 11.46 (d, J=1.6 Hz, 1H), 11.00 (s, 1H), 7.42 (d, J=7.8 Hz, 1H), 7.24 (d, J=7.8 Hz, 1H), 2.75-2.65 (m, 1H), 2.62-2.52 (m, 2H), 2.08-1.99 (m, 1H), 1.89 (s, 3H). LC/MS RT 0.46 min, m/z 327.3 [M−H]$^-$.

Example 5: Synthesis of 4-bromo-7-(3-methyl-2,6-dioxopiperidin-3-yl)-1,3-dihydroimidazo[4,5-e]isoindole-2,6,8(7H)-trione (Compound 5)

To the solution of 7-(3-methyl-2,6-dioxopiperidin-3-yl)-1,3-dihydroimidazo[4,5-e]isoindole-2,6,8(7H)-trione (3.0 mg, 9.1 μmop prepared in Example 4 in DMF (0.2 mL) was added NBS (4.2 mg, 0.023 mmol) at room temperature. After being stirred at 40° C. for 16 hours, the residue was directly purified by reverse phase preparative HPLC to give the title compound (1.5 mg, 40%) as a colorless solid.

$^1$H NMR (500 MHz, DMSO-$d_6$) δ 12.14 (s, 1H), 11.90 (s, 1H), 11.01 (s, 1H), 7.58 (s, 1H), 2.74-2.63 (m, 1H), 2.56 (m, 2H), 2.04 (m, 1H), 1.88 (s, 3H). LC/MS RT 0.60 min, m/z 405.2, 407.2 [M−H]$^-$.

Example 6: Synthesis of 8-(3-methyl-2,6-dioxopiperidin-3-yl)-1H-pyrrolo[3,4-f]quinoxaline-2,3,7,9(4H,8H)-tetraone (Compound 6)

8-(3-methyl-2,6-dioxopiperidin-3-yl)-1H-pyrrolo[3,4-f]quinoxaline-2,3,7,9(4H,8H)-tetraone was synthesized by the same procedure as Example 4 by using 2,3-dioxo-1,2,3,4-tetrahydroquinoxaline-5,6-dicarboxylic acid instead of 2-oxo-2,3-dihydro-1H-benzo[d]imidazole-4,5-dicarboxylic acid.

$^1$H NMR (500 MHz, DMSO-$d_6$) δ 12.42 (s, 1H), 11.05 (s, 1H), 10.50 (s, 1H), 7.56 (d, J=7.9 Hz, 1H), 7.43 (d, J=7.9 Hz, 1H), 2.73 (ddd, J=19.9, 12.4, 5.5 Hz, 1H), 2.61-2.52 (m, 2H), 2.13-2.00 (m, 1H), 1.91 (s, 3H). LC/MS RT 0.39 min, m/z 355.3 [M−H]$^-$.

Example 7: Synthesis of 7-(3-methyl-2,6-dioxopiperidin-3-yl)-2-thioxo-2,3-dihydroimidazo[4,5-e]isoindole-6,8(1H,7H)-dione (Compound 7)

7-(3-methyl-2,6-dioxopiperidin-3-yl)-2-thioxo-2,3-dihydroimidazo[4,5-e]isoindole-6,8(1H,7H)-dione was synthesized by the same procedure as Example 4 by using 2-thioxo-2,3-dihydro-1H-benzo[d]imidazole-4,5-dicarboxylic acid instead of 2-oxo-2,3-dihydro-1H-benzo[d]imidazole-4,5-dicarboxylic acid.

$^1$H NMR (500 MHz, DMSO-$d_6$) δ 13.54 (s, 1H), 13.25-13.21 (m, 1H), 11.02 (s, 1H), 7.56 (d, J=7.9 Hz, 1H), 7.43 (d, J=7.9 Hz, 1H), 2.76-2.64 (m, 1H), 2.62-2.52 (m, 2H), 2.10-2.01 (m, 1H), 1.90 (s, 3H). LC/MS RT 0.51 min, m/z 343.2 [M−H]$^-$.

Example 8: Synthesis of 6-bromo-2-(2,6-dioxopiperidin-3-yl)-4-hydroxyisoindoline-1,3-dione (Compound 8)

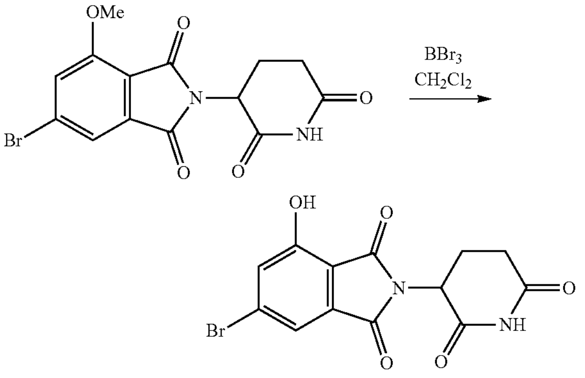

6-Bromo-2-(2,6-dioxopiperidin-3-yl)-4-methoxyisoindoline-1,3-dione was synthesized by the same procedure as Example 1 by using 5-bromo-3-methoxyphthalic acid instead of 2-oxo-2,3-dihydro-1H-benzo[d]imidazole-4,5-dicarboxylic acid. To a stirred suspension of 6-bromo-2-(2,6-dioxopiperidin-3-yl)-4-methoxyisoindoline-1,3-dione (359 mg, 0.977 mmol) in $CHCl_3$ (5 mL) was added $BBr_3$ (1.0 M in $CH_2Cl_2$, 1.96 mL) at room temperature. After being stirred at room temperature for 16 hours, ice water was added. After being stirred at 0° C. for 1 hour, precipitate was collected by filtration and washed the solid with water. The filtrate was purified by silica gel column chromatography (0 to 10% MeOH in DCM) to give the title compound (269 mg, 78%) as a colorless solid.

$^1$H NMR (500 MHz, DMSO-$d_6$) δ 11.69 (s, 1H), 11.11 (s, 1H), 7.50 (d, J=1.5 Hz, 1H), 7.42 (d, J=1.5 Hz, 1H), 5.09 (dd, J=12.9, 5.4 Hz, 1H), 2.88 (ddd, J=17.1, 13.9, 5.4 Hz, 1H), 2.63-2.52 (m, 2H), 2.03 (m, 1H). LC/MS RT 0.73 min, m/z 351.2, 353.1 [M−H]$^-$.

Example 9: Synthesis of 2-(2,6-dioxopiperidin-3-yl)-N-methyl-1,3-dioxoisoindoline-5-carboxamide (Compound 9)

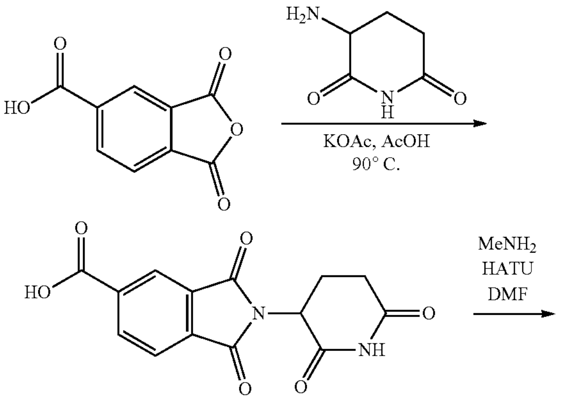

-continued

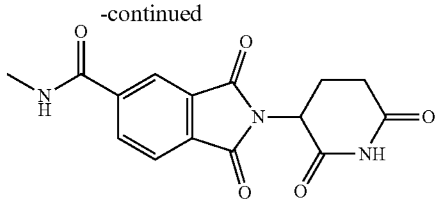

Synthesis of 2-(2,6-dioxopiperidin-3-yl)-1,3-dioxoisoindoline-5-carboxylic acid

A suspension mixture of 1,3-dioxo-1,3-dihydroisobenzofuran-5-carboxylic acid (10 mg, 0.052 mmol), 3-aminopiperidine-2,6-dione hydrochloride (8.6 mg, 0.052 mmol) and KOAc (15.3 mg, 0.16 mmol) in AcOH (0.2 mL) was stirred at 90° C. for 16 hours. After being cooled, the residue was directly purified by reverse phase preparative HPLC to quantitatively give 2-(2,6-dioxopiperidin-3-yl)-1,3-dioxoisoindoline-5-carboxylic acid as a gray solid.

$^1$H NMR (500 MHz, DMSO-$d_6$) δ 11.16 (s, 1H), 8.41 (dd, J=7.7, 1.4 Hz, 1H), 8.29 (d, J=1.4 Hz, 1H), 8.06 (d, J=7.7 Hz, 1H), 5.21 (dd, J=12.9, 5.4 Hz, 1H), 2.91 (ddd, J=17.1, 13.9, 5.4 Hz, 1H), 2.66-2.52 (m, 2H), 2.09 (m, 1H).

Synthesis of 2-(2,6-dioxopiperidin-3-yl)-N-methyl-1,3-dioxoisoindoline-5-carboxamide (Compound 9)

To the stirred mixture of 2-(2,6-dioxopiperidin-3-yl)-1,3-dioxoisoindoline-5-carboxylic acid (5.0 mg, 0.017 mmol) and HATU (12.5 mg, 0.033 mmol) in DMF (0.2 mL) was added $MeNH_2$ (2.0 M in THF, 40 μL). After being stirred at room temperature for 30 minutes, the residue was directly purified by reverse phase preparative HPLC to give the title compound (2.5 mg, 48%) as a colorless solid.

$^1$H NMR (500 MHz, DMSO-$d_6$) δ 11.15 (s, 1H), 8.87 (q, J=4.6 Hz, 1H), 8.33 (s, 1H), 8.33-8.30 (m, 1H), 8.04 (dd, J=7.5, 1.0 Hz, 1H), 5.20 (dd, J=12.9, 5.4 Hz, 1H), 2.90 (ddd, J=17.0, 13.8, 5.4 Hz, 1H), 2.84 (d, J=4.6 Hz, 3H), 2.67-2.52 (m, 2H), 2.09 (m, 1H). LC/MS RT 0.44 min, m/z 314.3 [M−H]$^-$.

Example 10: Synthesis of 2-(2,6-dioxopiperidin-3-yl)-4,7-dihydroxyisoindoline-1,3-dione (Compound 10)

2-(2,6-dioxopiperidin-3-yl)-4,7-dihydroxyisoindoline-1,3-dione was synthesized by the same procedure as Example 9 by using 4,7-dihydroxyisobenzofuran-1,3-dione instead of 1,3-dioxo-1,3-dihydroisobenzofuran-5-carboxylic acid.

$^1$H NMR (500 MHz, DMSO-$d_6$) δ 11.05 (s, 1H), 10.32 (s, 2H), 7.11 (s, 2H), 5.00 (dd, J=12.7, 5.4 Hz, 1H), 2.88 (ddd, J=16.9, 13.9, 5.4 Hz, 1H), 2.51-2.44 (m, 2H), 2.02-1.94 (m, 1H). LC/MS RT 0.37 min, m/z 289.2 [M−H]$^-$.

Example 11: Synthesis of 2-(2,6-dioxopiperidin-3-yl)-1,3-dioxoisoindoline-5-carboxamide (Compound 11)

2-(2,6-dioxopiperidin-3-yl)-1,3-dioxoisoindoline-5-carboxamide was synthesized by the same procedure as Example 9 by using ammonium hydroxide instead of methylamine.

$^1$H NMR (500 MHz, DMSO-$d_6$) δ 13.73 (s, 1H), 11.16 (s, 1H), 8.41 (dd, J=7.7, 1.4 Hz, 1H), 8.29 (d, J=1.4 Hz, 1H), 8.06 (d, J=7.7 Hz, 1H), 5.21 (ddd, J=12.8, 5.4, 1.5 Hz, 1H), 2.91 (ddd, J=17.0, 13.8, 5.4 Hz, 1H), 2.67-2.52 (m, 3H), 2.09 (m, 1H). LC/MS RT 0.47 min, m/z 301.3 [M−H]⁻.

Example 12: Synthesis of (R)-2-(3-methyl-2,6-dioxopiperidin-3-yl)-1,3-dioxoisoindoline-5-carboxylic acid (Compound 12)

(R)-2-(3-methyl-2,6-dioxopiperidin-3-yl)-1,3-dioxoisoindoline-5-carboxylic acid was synthesized by the same procedure as Example 9 by using (R)-3-amino-3-methylpiperidine-2,6-dione hydrobromide instead of 3-aminopiperidine-2,6-dione hydrochloride.

$^1$H NMR (500 MHz, DMSO-$d_6$) δ 13.77 (brs, 1H), 11.05 (s, 1H), 8.38 (dd, J=7.8, 1.4 Hz, 1H), 8.21 (d, J=1.4 Hz, 1H), 7.97 (d, J=7.8 Hz, 1H), 2.74-2.64 (m, 1H), 2.64-2.53 (m, 2H), 2.07 (m, 1H), 1.91 (s, 3H). LC/MS RT 0.55 min, m/z 315.3 [M−H]⁻.

Example 13: Synthesis of 2-(2,6-dioxopiperidin-3-yl)-4-hydroxy-5-(1H-pyrazol-4-yl)isoindoline-1,3-dione (Compound 13)

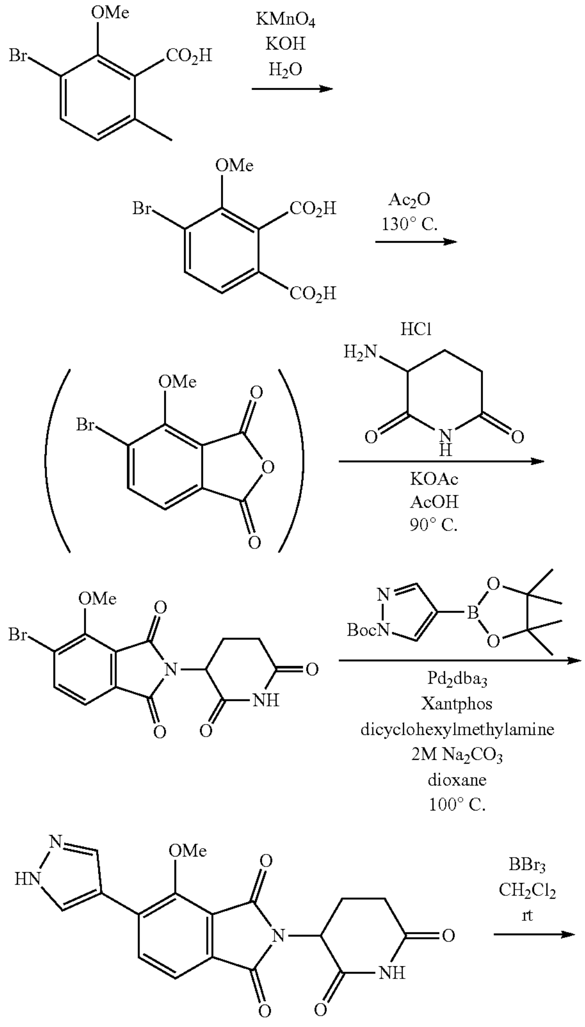

-continued

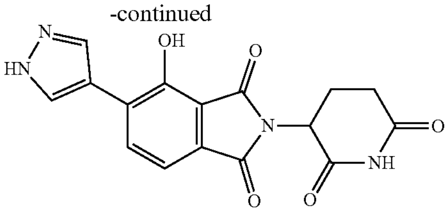

Synthesis of 4-bromo-3-methoxyphthalic acid

To the stirred solution of 3-bromo-2-methoxy-6-methylbenzoic acid (500 mg, 2.0 mmol) and KOH (572 mg, 10 mmol) in water (20 mL) was added potassium permanganase (967 mg, 6.1 mmol) at room temperature. After being stirred at 70° C. for 3 days, $NaHSO_3$ (637 mg, 6.1 mmol) was added at room temperature. The stirred mixture was carefully acidified with 6M HCl. The precipitate was then collected by filtration and washed with water to give the title compound as a colorless solid (426 mg, 76%). 1H NMR (500 MHz, DMSO-$d_6$) δ 7.66 (d, J=8.4 Hz, 1H), 7.55 (d, J=8.4 Hz, 1H), 3.81 (s, 3H).

Synthesis of 5-bromo-2-(2,6-dioxopiperidin-3-yl)-4-methoxyisoindoline-1,3-dione A suspension of 4-bromo-3-methoxyphthalic acid (200 mg, 0.73 mmol) in acetic anhydride (2 mL) was stirred at 130° C. for 5 hours and then cooled down to room temperature. The stirred mixture was diluted with EtOAc and the precipitate was filtered off. The filtrate was evaporated with EtOAc and dried in vacuo to give a crude compound as a dark purple solid. The mixture of crude 5-bromo-4-methoxyisobenzofuran-1,3-dione, 3-aminopiperidine-2,6-dione hydrochloride (132 mg, 0.80 mmol) and potassium acetate (215 mg, 2.2 mmol) in AcOH (5 mL) was stirred at 100° C. for 16 hours. The reaction mixture was cooled and partitioned between EtOAc and water. Organic layer was separated, washed with water then concentrated. The residue was purified by silica gel column chromatography (0 to 10% MeOH in DCM) to give the title compound (201 mg, 75%) as a dark orange solid. 1H NMR (500 MHz, DMSO-$d_6$) δ 11.14 (s, 1H), 8.15 (d, J=7.8 Hz, 1H), 7.57 (d, J=7.8 Hz, 1H), 5.16 (dd, J=12.9, 5.4 Hz, 1H), 4.08 (s, 3H), 2.89 (ddd, J=17.2, 13.9, 5.5 Hz, 1H), 2.66-2.51 (m, 2H), 2.06 (m, 1H).

Synthesis of 2-(2,6-dioxopiperidin-3-yl)-4-hydroxy-5-(1H-pyrazol-4-yl)isoindoline-1,3-dione (Compound 13)

A mixture of 5-bromo-2-(2,6-dioxopiperidin-3-yl)-4-methoxyisoindoline-1,3-dione (5.0 mg, 0.014 mmol), tert-butyl 4-(4,4,5,5-tetramethyl-1,3,2-dioxaborolan-2-yl)-1H-pyrazole-1-carboxylate (16 mg, 0.054 mmol), bis (dibenzylideneacetone)palladium (1.2 mg, 0.0014 mmol), 4,5-Bis(diphenylphosphino)-9,9-dimethylxanthene (1.6 mmol, 0.0028 mmol), dicyclohexylmethylamine (5.8 μL, 0.027 mmol) and 2M $Na_2CO_3$ (6.8 μL, 0.014 mmol) in 1,4-dioxane (0.2 mL) was stirred at 100° C. for 16 hours. The reaction mixture was purified by silica gel column chromatography (0-10% MeOH in DCM) to give crude 2-(2,6-dioxopiperidin-3-yl)-4-methoxy-5-(1H-pyrazol-4-yl) isoindoline-1,3-dione as a pale brown gum. To the solution of the crude product in DCM (0.1 mL) was added boron-tribromide (1.0 M in DCM, 0.1 mL) at room temperature.

After being stirred at room temperature for 16 hours, reaction was quenched by the addition of water and the volatiles were removed under reduced pressure. The residue was purified by reverse phase preparative HPLC to give the title compound (1.1 mg, 24% in 2 steps) as a pale yellow solid. $^1$H NMR (500 MHz, DMSO-$d_6$) δ 11.05 (s, 1H), 10.32 (s, 1H), 8.17 (brs, 2H), 7.98 (d, J=7.6 Hz, 1H), 7.34 (d, J=7.6 Hz, 1H), 5.04 (dd, J=12.7, 5.4 Hz, 1H), 2.83 (ddd, J=16.8, 13.5, 5.4 Hz, 1H), 2.57-2.45 (m, 2H), 2.04-1.94 (m, 1H). LC/MS RT 0.54 min, m/z 339.3 $[M-H]^-$.

Example 14: Synthesis of 2-(2,6-dioxopiperidin-3-yl)-4-methoxy-6-(1H-pyrazol-4-yl)isoindoline-1,3-dione (Compound 14)

2-(2,6-Dioxopiperidin-3-yl)-4-methoxy-6-(1H-pyrazol-4-yl)isoindoline-1,3-dione was synthesized by the same procedure as Example 13 by using 4-bromo-2-methoxy-6-methylbenzoic acid instead of 3-bromo-2-methoxy-6-methylbenzoic acid.

$^1$H NMR (500 MHz, DMSO-$d_6$) δ 13.22 (s, 1H), 11.10 (s, 1H), 8.60 (s, 1H), 8.25 (s, 1H), 7.76 (d, J=1.2 Hz, 1H), 7.68 (d, J=1.2 Hz, 1H), 5.09 (dd, J=12.8, 5.5 Hz, 1H), 4.04 (s, 3H), 2.90 (ddd, J=16.8, 13.8, 5.3 Hz, 1H), 2.64-2.56 (m, 2H), 2.07-2.00 (m, 1H). LC/MS RT 0.55 min, m/z 353.3 $[M-H]^-$.

Example 15: Synthesis of 2-(2,6-dioxopiperidin-3-yl)-4-hydroxy-6-(1H-pyrazol-4-yl)isoindoline-1,3-dione (Compound 15)

2-(2,6-Dioxopiperidin-3-yl)-4-hydroxy-6-(1H-pyrazol-4-yl)isoindoline-1,3-dione was synthesized by the same procedure as Example 13 by using 2-(2,6-dioxopiperidin-3-yl)-4-methoxy-6-(1H-pyrazol-4-yl)isoindoline-1,3-dione as a starting material.

$^1$H NMR (500 MHz, DMSO-$d_6$) δ 11.11 (s, 1H), 11.09 (s, 1H), 8.25 (s, 2H), 7.63 (d, J=1.3 Hz, 1H), 7.39 (d, J=1.3 Hz, 1H), 5.08 (dd, J=12.7, 5.4 Hz, 1H), 2.90 (ddd, J=16.5, 13.5, 5.2 Hz, 1H), 2.65-2.51 (m, 2H), 2.06-1.99 (m, 1H). LC/MS RT 0.47 min, m/z 339.3 $[M-H]^-$.

Example 16: Synthesis of 2-(2,6-dioxopiperidin-3-yl)-4-hydroxy-6-(1-methyl-1H-pyrazol-4-yl)isoindoline-1,3-dione (Compound 16)

2-(2,6-Dioxopiperidin-3-yl)-4-hydroxy-6-(1-methyl-1H-pyrazol-4-yl)isoindoline-1,3-dione was synthesized by the same procedure as Example 15 by using 1-methyl-4-(4,4,5,5-tetramethyl-1,3,2-dioxaborolan-2-yl)-1H-pyrazole instead of tert-butyl 4-(4,4,5,5-tetramethyl-1,3,2-dioxaborolan-2-yl)-1H-pyrazole-1-carboxylate.

$^1$H NMR (500 MHz, DMSO-$d_6$) δ 11.13 (s, 1H), 11.09 (s, 1H), 8.36 (s, 1H), 8.00 (s, 1H), 7.57 (d, J=1.3 Hz, 1H), 7.33 (d, J=1.3 Hz, 1H), 5.08 (dd, J=12.7, 5.4 Hz, 1H), 3.89 (s, 3H), 2.89 (ddd, J=16.8, 13.7, 5.4 Hz, 1H), 2.63-2.52 (m, 2H), 2.03 (m, 1H). LC/MS RT 0.56 min, m/z 355.3 $[M+H]^+$.

Example 17: Synthesis of 2-(2,6-dioxopiperidin-3-yl)-4-hydroxy-6-(1H-pyrazol-5-yl)isoindoline-1,3-dione (Compound 17)

2-(2,6-Dioxopiperidin-3-yl)-4-hydroxy-6-(1H-pyrazol-5-yl)isoindoline-1,3-dione was synthesized by the same procedure as Example 15 by using 1-(tetrahydro-2H-pyran-2-yl)-5-(4,4,5,5-tetramethyl-1,3,2-dioxaborolan-2-yl)-1H-pyrazole instead of tert-butyl 4-(4,4,5,5-tetramethyl-1,3,2-dioxaborolan-2-yl)-1H-pyrazole-1-carboxylate.

$^1$H NMR (500 MHz, DMSO-$d_6$) δ 11.23 (s, 1H), 11.10 (s, 1H), 7.85 (d, J=2.3 Hz, 1H), 7.75 (s, 1H), 7.73 (s, 1H), 6.92 (d, J=2.3 Hz, 1H), 5.09 (dd, J=12.7, 5.5 Hz, 1H), 2.90 (ddd, J=16.7, 13.7, 5.3 Hz, 1H), 2.64-2.53 (m, 2H), 2.11-2.00 (m, 1H). LC/MS RT 0.52 min, m/z 339.3 $[M-H]^-$.

Example 18: Synthesis of 2-(2,6-dioxopiperidin-3-yl)-4-hydroxy-6-(1-methyl-1H-pyrazol-3-yl)isoindoline-1,3-dione (Compound 18)

2-(2,6-Dioxopiperidin-3-yl)-4-hydroxy-6-(1-methyl-1H-pyrazol-3-yl)isoindoline-1,3-dione was synthesized by the same procedure as Example 15 by using 1-methyl-3-(4,4,5,5-tetramethyl-1,3,2-dioxaborolan-2-yl)-1H-pyrazole instead of tert-butyl 4-(4,4,5,5-tetramethyl-1,3,2-dioxaborolan-2-yl)-1H-pyrazole-1-carboxylate.

$^1$H NMR (500 MHz, DMSO-$d_6$) δ 11.21 (s, 1H), 11.10 (s, 1H), 7.82 (d, J=2.3 Hz, 1H), 7.70 (s, 2H), 6.90 (d, J=2.3 Hz, 1H), 5.09 (dd, J=12.7, 5.5 Hz, 1H), 3.93 (s, 3H), 2.90 (ddd, J=16.7, 13.7, 5.4 Hz, 1H), 2.66-2.53 (m, 2H), 2.03 (m, 1H). LC/MS RT 0.61 min, m/z 355.4 $[M+H]^+$.

Example 19: Synthesis of 2-(2,6-dioxopiperidin-3-yl)-5-(6-oxo-1,6-dihydropyridin-3-yl)isoindoline-1,3-dione (Compound 19)

2-(2,6-Dioxopiperidin-3-yl)-5-(6-oxo-1,6-dihydropyridin-3-yl)isoindoline-1,3-dione was synthesized by the same procedure as Example 13 by using 5-bromo-2-(2,6-dioxopiperidin-3-yl)isoindoline-1,3-dione instead of 5-bromo-2-(2,6-dioxopiperidin-3-yl)-4-methoxyisoindoline-1,3-di one and 2-methoxy-5-(4,4,5,5-tetramethyl-1,3,2-dioxaborolan-2-yl)pyridine instead of tert-butyl 4-(4,4,5,5-tetramethyl-1,3,2-dioxaborolan-2-yl)-1H-pyrazole-1-carboxylate.

$^1$H NMR (500 MHz, DMSO-$d_6$) δ 12.01 (s, 1H), 11.06 (s, 1H), 8.07 (d, J=1.7 Hz, 1H), 8.01 (dd, J=7.9, 1.7 Hz, 1H), 7.98 (d, J=2.9 Hz, 1H), 7.95 (dd, J=9.5, 2.9 Hz, 1H), 7.85 (d, J=7.9 Hz, 1H), 6.40 (d, J=9.5 Hz, 1H), 5.10 (ddd, J=12.8, 5.4, 1.5 Hz, 1H), 2.83 (ddd, J=17.2, 13.8, 5.4 Hz, 1H), 2.58-2.45 (m, 2H), 2.04-1.96 (m, 1H). LC/MS RT 0.48 min, m/z 352.4 $[M+H]^+$.

Example 20: Synthesis of 2-(2,6-dioxopiperidin-3-yl)-5-hydroxy-6-(1H-pyrazol-4-yl)isoindoline-1,3-dione (Compound 20)

2-(2,6-Dioxopiperidin-3-yl)-5-hydroxy-6-(1H-pyrazol-4-yl)isoindoline-1,3-dione was synthesized by the same procedure as Example 13 by using 1-bromo-2-methoxy-4,5-dimethylbenzene instead of 3-bromo-2-methoxy-6-methylbenzoic acid.

$^1$H NMR (500 MHz, DMSO-$d_6$) δ 11.43 (s, 1H), 11.10 (s, 1H), 8.33 (s, 2H), 8.15 (s, 1H), 7.33 (s, 1H), 5.10 (dd, J=12.7, 5.3 Hz, 1H), 2.90 (ddd, J=17.4, 13.6, 5.3 Hz, 1H), 2.62-2.55 (m, 2H), 2.07-2.01 (m, 1H). LC/MS RT 0.54 min, m/z 339.3 $[M-H]^-$.

Example 21: Synthesis of 2-(3-benzyl-2,6-dioxopiperidin-3-yl)-4-hydroxy-5-(1H-pyrazol-4-yl)isoindoline-1,3-dione (Compound 21)

2-(3-Benzyl-2,6-dioxopiperidin-3-yl)-4-hydroxy-5-(1H-pyrazol-4-yl)isoindoline-1,3-dione was synthesized by the same procedure as Example 13 by using 3-amino-3-benzylpiperidine-2,6-dione hydrochloride instead of 3-aminopiperidine-2,6-dione hydrochloride.

$^1$H NMR (500 MHz, DMSO-$d_6$) δ 10.99 (s, 1H), 10.28 (s, 1H), 8.21 (s, 2H), 8.01 (d, J=7.6 Hz, 1H), 7.30 (d, J=7.6, 1H), 7.27-7.18 (m, 5H), 3.79 (d, J=13.5 Hz, 1H), 3.46 (d, J=13.5 Hz, 1H), 2.91-2.85 (m, 1H), 2.54-2.37 (m, 2H), 2.00 (m, 1H). LC/MS RT 0.93 min, m/z 431.5 $[M+H]^+$.

Example 22: Synthesis of (R)-4-hydroxy-2-(3-methyl-2,6-dioxopiperidin-3-yl)-5-(1H-pyrazol-4-yl) isoindoline-1,3-dione (Compound 22)

(R)-4-hydroxy-2-(3-methyl-2,6-dioxopiperidin-3-yl)-5-(1H-pyrazol-4-yl)isoindoline-1,3-dione was synthesized by the same procedure as Example 13 by using (R)-3-amino-3-methylpiperidine-2,6-dione hydrobromide instead of 3-aminopiperidine-2,6-dione hydrochloride.

$^1$H NMR (500 MHz, DMSO-$d_6$) δ 13.12 (brs, 1H), 11.02 (s, 1H), 10.27 (s, 1H), 8.37-8.08 (m, 2H), 8.03 (d, J=7.6 Hz, 1H), 7.33 (d, J=7.6 Hz, 1H), 2.76-2.65 (m, 1H), 2.62-2.52 (m, 2H), 2.10-2.01 (m, 1H), 1.90 (s, 3H). LC/MS RT 0.61 min, m/z 355.1 $[M+H]^+$.

Example 23: Synthesis of 2-(3-benzyl-2,6-dioxopiperidin-3-yl)-4-hydroxyisoindoline-1,3-dione (Compound 23)

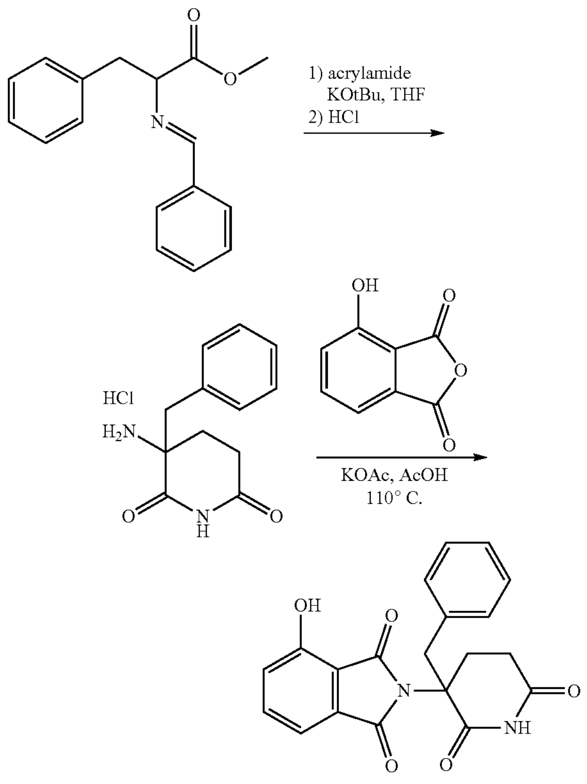

Synthesis of 3-amino-3-benzylpiperidine-2,6-dione hydrochloride

To a stirred mixture of methyl-2-(benzylideneamino)-3-phenylpropanoate (1.0 g, 3.7 mmol) and acrylamide (319 mg, 4.5 mmol) in THF (15 mL) was added KOtBu (504 mg, 4.5 mmol) in 3 portions at 0° C. After being stirred at room temperature for 2 hours, reaction was quenched by the addition of water. Reaction mixture was partitioned between EtOAc and water, and organic layer was washed with water then concentrated. The crude residue was dissolved in dioxane (15 mL) and 6M HCl (2 mL) was added to the stirred solution. After being stirred at room temperature for 30 minutes then concentrated, the residue was triturated with EtOAc and small amount of MeOH to give a colorless solid. (944 mg, 99% in 2 steps)

$^1$H NMR (500 MHz, DMSO-$d_6$) δ 11.39 (s, 1H), 8.79 (s, 3H), 7.40-7.27 (m, 5H), 3.36 (d, J=14.1 Hz, 1H), 3.20 (d, J=14.1 Hz, 1H), 2.87 (ddd, J=18.2, 12.7, 6.0 Hz, 1H), 2.67 (ddd, J=18.2, 5.7, 3.0 Hz, 1H), 2.23 (m, 1H), 2.06 (ddd, J=13.7, 6.0, 3.0 Hz, 1H).

Synthesis of 2-(3-benzyl-2,6-dioxopiperidin-3-yl)-4-hydroxyisoindoline-1,3-dione (Compound 23)

A mixture of 3-amino-3-benzylpiperidine-2,6-dione hydrochloride (10 mg, 0.039 mmol), 4-hydroxyisobenzofuran-1,3-dione (6.5 mg, 0.039 mmol) and KOAc (7.7 mg, 0.078 mmol) and AcOH (0.2 mL) was stirred at 110° C. for 16 hours. After being cooled, the residue was directly purified by reverse phase preparative HPLC to give the title compound (7.4 mg, 52%) as a colorless solid.

$^1$H NMR (500 MHz, DMSO-$d_6$) δ 10.88 (s, 2H), 7.54 (dd, J=8.4, 7.2 Hz, 1H), 7.18-7.08 (m, 7H), 3.68 (d, J=13.5 Hz, 1H), 3.35 (d, J=13.5 Hz, 1H), 2.82-2.74 (m, 1H), 2.43-2.30 (m, 5H), 1.89 (ddd, J=14.4, 11.5, 5.6 Hz, 1H). LC/MS RT 0.93 min, m/z 363.3 $[M-H]^-$.

Example 24: Synthesis of 2-(3-ethyl-2,6-dioxopiperidin-3-yl)-4-hydroxyisoindoline-1,3-dione (Compound 24)

2-(3-Ethyl-2,6-dioxopiperidin-3-yl)-4-hydroxyisoindoline-1,3-dione was synthesized by the same procedure as Example 23 by using methyl-2-(benzylideneamino) butanoate instead of methyl-2-(benzylideneamino)-3-phenyl propanoate.

$^1$H NMR (500 MHz, DMSO-$d_6$) δ 11.09 (s, 1H), 10.93 (s, 1H), 7.63 (dd, J=8.3, 7.0 Hz, 1H), 7.25 (d, J=7.0 Hz, 1H), 7.21 (d, J=8.3 Hz, 1H), 2.64-2.51 (m, 3H), 2.42-2.33 (m, 1H), 2.32-2.25 (m, 1H), 2.10-2.01 (m, 1H), 0.92 (t, J=7.2 Hz, 3H). LC/MS RT 0.68 min, m/z 301.3 $[M-H]^-$.

Example 25: Synthesis of 2-(3-ethyl-2,6-dioxopiperidin-3-yl)-5-hydroxyisoindoline-1,3-dione (Compound 25)

2-(3-Ethyl-2,6-dioxopiperidin-3-yl)-5-hydroxyisoindoline-1,3-dione was synthesized by the same procedure as Example 24 by using 5-hydroxyisobenzofuran-1,3-dione instead of 4-hydroxyisobenzofuran-1,3-dione.

$^1$H NMR (500 MHz, DMSO-$d_6$) δ 10.99 (s, 1H), 10.95 (s, 1H), 7.68 (d, J=8.2 Hz, 1H), 7.15 (dd, J=8.2, 2.1 Hz, 1H), 7.11 (d, J=2.1 Hz, 1H), 2.65-2.52 (m, 3H), 2.40-2.24 (m, 2H), 2.11-2.00 (m, 1H), 0.91 (t, J=7.2 Hz, 3H). LC/MS RT 0.70 min, m/z 301.3 $[M-H]^-$.

Example 26: Synthesis of 4-hydroxy-2-(3-isopropyl-2,6-dioxopiperidin-3-yl)isoindoline-1,3-dione (Compound 26)

4-Hydroxy-2-(3-isopropyl-2,6-dioxopiperidin-3-yl)isoindoline-1,3-dione was synthesized by the same procedure as Example 23 by using methyl-2-(benzylideneamino)-3-methylbutanoate instead of methyl-2-(benzylideneamino)-3-phenyl propanoate.

$^1$H NMR (500 MHz, DMSO-$d_6$) δ 11.10 (s, 1H), 10.77 (s, 1H), 7.56 (dd, J=8.4, 7.2 Hz, 1H), 7.19 (d, J=7.2 Hz, 1H), 7.15 (d, J=8.4 Hz, 1H), 2.74-2.57 (m, 2H), 2.50-2.40 (m, 1H), 2.35 (dd, J=9.1, 3.8 Hz, 2H), 2.12 (dt, J=14.2, 9.1 Hz, 1H), 0.98 (d, J=6.8 Hz, 3H), 0.93 (d, J=6.9 Hz, 3H). LC/MS RT 0.53 min, m/z 350.3 $[M-H]^-$.

Example 27: Synthesis of methyl 4-((3-(4-hydroxy-1,3-dioxoisoindolin-2-yl)-2,6-dioxopiperidin-3-yl)methyl)benzoate (Compound 27)

Methyl 4-((3-(4-hydroxy-1,3-dioxoisoindolin-2-yl)-2,6-dioxopiperidin-3-yl)methyl)benzoate was synthesized by the same procedure as Example 23 by using methyl-4-(2-(benzylideneamino)-3-methoxy-3-oxopropyl)benzoate instead of methyl-2-(benzylideneamino)-3-phenylpropanoate.

$^1$H NMR (500 MHz, DMSO-$d_6$) δ 11.11 (s, 1H), 10.98 (s, 1H), 7.81 (d, J=7.8 Hz, 2H), 7.62 (dd, J=8.4, 7.2 Hz, 1H), 7.39 (d, J=7.8 Hz, 2H), 7.21 (m, 2H), 3.82 (s, 3H), 3.77 (d, J=13.5 Hz, 1H), 3.51 (d, J=13.5 Hz, 1H), 2.90 (dt, J=14.3, 4.4 Hz, 1H), 2.50-2.38 (m, 2H), 1.98 (ddd, J=14.3, 10.6, 6.5 Hz, 1H). LC/MS RT 0.92 min, m/z 421.4 $[M-H]^-$.

Example 28: Synthesis of N-(2-(2,6-dioxopiperidin-3-yl)-1,3-dioxoisoindolin-5-yl)methanesulfonamide (Compound 28)

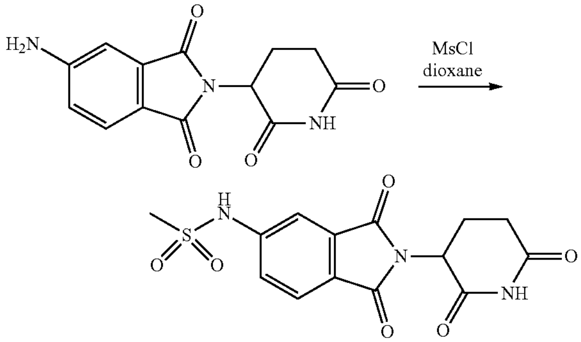

To a stirred solution of 5-amino-2-(2,6-dioxopiperidin-3-yl)isoindoline-1,3-dione (10.0 mg, 0.037 mmol) in dioxane (0.2 mL) was added MsCl (6.4 μL, 0.040 mmol) at room temperature. After being stirred at 90° C. for 16 hours, the residue was directly purified by reverse phase preparative HPLC to give the title compound (6.9 mg, 54%) as a yellow solid.

$^1$H NMR (500 MHz, DMSO-$d_6$) δ 11.12 (s, 1H), 7.91 (d, J=8.1 Hz, 1H), 7.65 (d, J=1.9 Hz, 1H), 7.58 (dd, J=8.1, 1.9 Hz, 1H), 5.14 (dd, J=12.9, 5.4 Hz, 1H), 3.19 (s, 3H), 2.89 (ddd, J=17.0, 13.8, 5.4 Hz, 1H), 2.65-2.52 (m, 2H), 2.05 (dtd, J=13.1, 5.4, 2.3 Hz, 1H). LC/MS RT 0.53 min, m/z 350.3 $[M-H]^-$.

Example 29: Synthesis of 2-(2,6-dioxopiperidin-3-yl)-5-(1H-pyrazol-4-yl)isoindoline-1,3-dione (Compound 29)

A mixture of 5-bromo-2-(2,6-dioxopiperidin-3-yl)isoindoline-1,3-dione (10.0 mg, 0.034 mmol), tert-butyl 4-(4,4,5,5-tetramethyl-1,3,2-dioxaborolan-2-yl)-1H-pyrazole-1-carboxylate (20.1 mg, 0.068 mmol), bis(dibenzylideneacetone)palladium (3.1 mg, 0.0034 mmol), 4,5-bis(diphenylphosphino)-9,9-dimethylxanthene (4.0 mg, 0.0068 mmol), dicyclohexylmethylamine (14.5 μL, 0.068 mmol) and 2M $Na_2CO_3$ (17.1 μL, 0.068 mmol) in 1,4-dioxane (0.3 mL) was stirred at 100° C. for 16 hours. The reaction mixture was directly purified by reverse phase preparative HPLC to give the title compound (3.3 mg, 30%) as a colorless solid.

$^1$H NMR (500 MHz, DMSO-$d_6$) δ 13.08 (s, 1H), 11.06 (s, 1H), 8.31 (s, 1H), 8.13 (d, J=1.5 Hz, 1H), 8.05 (dd, J=7.8, 1.5 Hz, 1H), 7.82 (d, J=7.8 Hz, 1H), 5.09 (dd, J=12.8, 5.3 Hz, 1H), 2.83 (ddd, J=17.0, 13.8, 5.3 Hz, 1H), 2.58-2.49 (m, 2H), 2.00 (m, 1H). LC/MS RT 0.55 min, m/z 323.3 $[M-H]^-$.

Example 30: Synthesis of (R)-2-(3-methyl-2,6-dioxopiperidin-3-yl)-5-(5-thioxo-4,5-dihydro-1,3,4-oxadiazol-2-yl)isoindoline-1,3-dione (Compound 30)

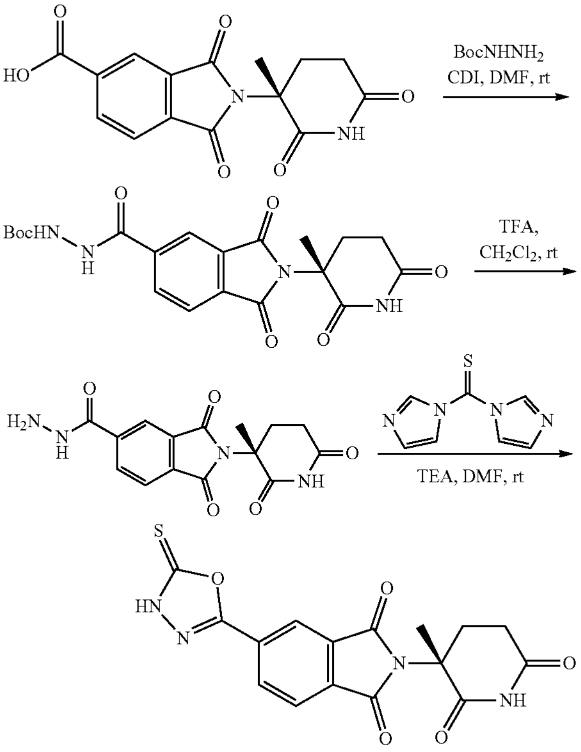

Synthesis of tert-butyl (R)-2-(2-(3-methyl-2,6-dioxopiperidin-3-yl)-1,3-dioxoisoindoline-5-carbonyl)hydrazine-1-carboxylate A mixture of (R)-2-(3-methyl-2,6-dioxopiperidin-3-yl)-1,3-dioxoisoindoline-5-carboxylic acid (8.5 mg, 0.027 mmol) and 1,1'-carbonyldiimidazole (6.5 mg, 0.040 mmol) in DMF was stirred at room temperature for 1 hour. After cooling down to 0° C., tert-butyl hydrazinecarboxylate (10.8 mg, 0.081 mmol) in THF (0.6 mL) was added to the stirred mixture. After being stirred at ambient temperature for 16 hours, the reaction mixture was partitioned between DCM and water. Organic layer was separated and concentrated.

The residue was purified by silica gel column chromatography (0 to 10% MeOH in DCM) to give the title compound (11 mg, 75%) as a colorless gum. $^1$H NMR (500 MHz, Methanol-d4) δ 8.29 (d, J=7.4, 1H), 8.28 (S, 1H), 7.97 (d, J=7.4 Hz, 1H), 2.85-2.71 (m, 2H), 2.71-2.60 (m, 1H), 2.22-2.12 (m, 1H), 2.05 (s, 3H), 1.52 (s, 3H).

Synthesis of (R)-2-(3-methyl-2,6-dioxopiperidin-3-yl)-5-(5-thioxo-4,5-dihydro-1,3,4-oxadiazol-2-yl)isoindoline-1,3-dione (Compound 30)

To a stirred solution of tert-butyl (R)-2-(2-(3-methyl-2,6-dioxopiperidin-3-yl)-1,3-dioxoisoindoline-5-carbonyl)hydrazine-1-carboxylate (11 mg, 0.026 mmol) in DCM (0.2 mL) was added TFA (0.1 mL) at room temperature. After being stirred at room temperature for 1 hour, volatiles were removed under reduced pressure to give a crude product. To a stirred solution of crude (R)-2-(3-methyl-2,6-dioxopiperidin-3-yl)-1,3-dioxoisoindoline-5-carbohydrazide and 1,1'-thiocarbonyldiimidazole (7.2 mg, 0.038 mmol) in DMF (0.2 mL) was added TEA (31.2 μL, 0.22 mmol) at room temperature. After being stirred at 80° C. for 16 hours, the reaction mixture was purified by reverse phase preparative HPLC to give the title compound (1.3 mg, 14% in 2 steps) as a pale yellow solid. $^1$H NMR (500 MHz, DMSO-$d_6$) δ 11.06 (s, 1H), 8.30 (dd, J=7.8, 1.5 Hz, 1H), 8.14 (d, J=1.5 Hz, 1H), 8.03 (d, J=7.8 Hz, 1H), 2.70 (ddd, J=18.4, 10.5, 5.4 Hz, 1H), 2.65-2.54 (m, 2H), 2.13-2.04 (m, 1H), 1.92 (s, 3H). LC/MS RT 0.74 min, m/z 373.4 [M+H]$^+$.

Example 31: Synthesis of 2-(2,6-dioxopiperidin-3-yl)-5-(5-oxo-4,5-dihydro-1,3,4-oxadiazol-2-yl)isoindoline-1,3-dione (Compound 31)

2-(2,6-Dioxopiperidin-3-yl)-5-(5-oxo-4,5-dihydro-1,3,4-oxadiazol-2-yl)isoindoline-1,3-dione was synthesized by the same procedure as Example 30 by using 1,3-dioxo-1,3-dihydroisobenzofuran-5-carboxylic acid instead of (R)-2-(3-methyl-2,6-dioxopiperidin-3-yl)-1,3-dioxoisoindoline-5-carboxylic acid and 1,1'-carbonyldiimidazole instead of 1,1'-thiocarbonyldiimidazole.

$^1$H NMR (500 MHz, DMSO-$d_6$) δ 12.09 (s, 1H), 11.08 (s, 1H), 9.09 (d, J=7.6 Hz, 1H), 9.07 (d, J=7.6 Hz, 1H), 7.97 (t, J=7.6 Hz, 1H), 5.11 (dd, J=12.8, 5.5 Hz, 1H), 2.82 (ddd, J=17.1, 13.9, 5.4 Hz, 1H), 2.58-2.45 (m, 2H), 2.01 (m, 1H). LC/MS RT 0.53 min, m/z 341.3 [M−H]$^-$.

Example 32: Synthesis of 2-(2,6-dioxopiperidin-3-yl)-4-(5-oxo-4,5-dihydro-1,3,4-oxadiazol-2-yl)isoindoline-1,3-dione (Compound 32)

2-(2,6-Dioxopiperidin-3-yl)-4-(5-oxo-4,5-dihydro-1,3,4-oxadiazol-2-yl)isoindoline-1,3-dione was synthesized by the same procedure as Example 30 by using 2-(2,6-dioxopiperidin-3-yl)-1,3-dioxoisoindoline-4-carboxylic acid instead of (R)-2-(3-methyl-2,6-dioxopiperidin-3-yl)-1,3-dioxoisoindoline-5-carboxylic acid and 1,1'-carbonyldiimidazole instead of 1,1'-thiocarbonyldiimidazole.

$^1$H NMR (500 MHz, DMSO-$d_6$) δ 12.88 (s, 1H), 11.09 (s, 1H), 8.18 (dd, J=7.9, 1.3 Hz, 1H), 8.08 (d, J=1.3 Hz, 1H), 8.02 (d, J=7.9 Hz, 1H), 5.13 (dd, J=12.9, 5.4 Hz, 1H), 2.83 (ddd, J=17.0, 13.8, 5.4 Hz, 1H), 2.58-2.44 (m, 2H), 2.02 (m, 1H). LC/MS RT 0.52 min, m/z 341.3 [M−H]$^-$.

Example 33: Synthesis of 2-(2,6-dioxopiperidin-3-yl)-5-(5-thioxo-4,5-dihydro-1,3,4-oxadiazol-2-yl)isoindoline-1,3-dione (Compound 33)

2-(2,6-Dioxopiperidin-3-yl)-5-(5-thioxo-4,5-dihydro-1,3,4-oxadiazol-2-yl)isoindoline-1,3-dione was synthesized by the same procedure as Example 30 by using 2-(2,6-dioxopiperidin-3-yl)-1,3-dioxoisoindoline-5-carboxylic acid instead of (R)-2-(3-methyl-2,6-dioxopiperidin-3-yl)-1,3-dioxoisoindoline-5-carboxylic acid.

$^1$H NMR (500 MHz, DMSO-$d_6$) δ 11.17 (s, 1H), 8.34 (dd, J=7.8, 1.5 Hz, 1H), 8.22 (d, J=1.5 Hz, 1H), 8.12 (d, J=7.8 Hz, 1H), 5.22 (ddd, J=12.8, 5.4, 1.5 Hz, 1H), 2.97-2.83 (m, 1H), 2.67-2.52 (m, 2H), 2.10 (m, 1H). LC/MS RT 0.66 min, m/z 357.3 [M−H]$^-$.

Example 34: Synthesis of 2-(2,6-dioxopiperidin-3-yl)-4-(5-thioxo-4,5-dihydro-1,3,4-oxadiazol-2-yl)isoindoline-1,3-dione (Compound 34)

2-(2,6-Dioxopiperidin-3-yl)-4-(5-thioxo-4,5-dihydro-1,3,4-oxadiazol-2-yl)isoindoline-1,3-dione was synthesized by the same procedure as Example 33 by using 2-(2,6-dioxopiperidin-3-yl)-1,3-dioxoisoindoline-4-carboxylic acid instead of 2-(2,6-dioxopiperidin-3-yl)-1,3-dioxoisoindoline-5-carboxylic acid.

$^1$H NMR (500 MHz, DMSO-$d_6$) δ 11.09 (s, 1H), 8.15 (dd, J=7.8, 1.0 Hz, 1H), 8.11 (dd, J=7.5, 1.0 Hz, 1H), 8.08-7.92 (dd, J=7.8, 7.5 Hz, 1H), 5.13 (dd, J=12.8, 5.5 Hz, 1H), 2.82 (ddd, J=17.1, 13.9, 5.5 Hz, 1H), 2.59-2.48 (m, 2H), 2.01 (m, 1H). LC/MS RT 0.64 min, m/z 357.2 [M−H]$^-$.

Example 35: Synthesis of 4-amino-2-(3-benzyl-2,6-dioxopiperidin-3-yl)isoindoline-1,3-dione (Compound 35)

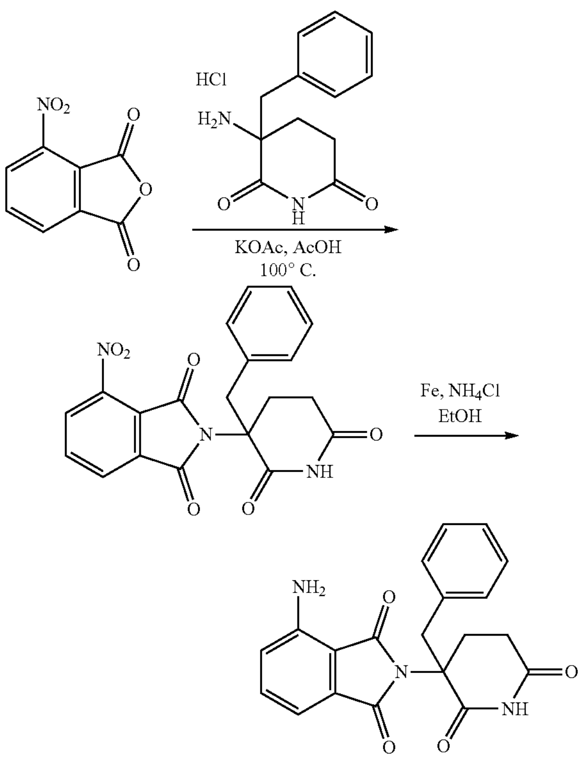

A mixture of 4-nitroisobenzofuran-1,3-dione (20 mg, 0.10 mmol) and 3-amino-3-benzylpiperidine-2,6-dione hydrochloride (26.4 mg, 0.10 mmol), KOAc (20.4 mg, 0.21 mmol) in AcOH (0.3 mL) was stirred at 100° C. for 40 hours. After cooling, water was added and the precipitate was collected by filtration to give crude 2-(3-benzyl-2,6-dioxopiperidin-3-yl)-4-nitroisoindoline-1,3-dione (22 mg). A mixture of crude 2-(3-benzyl-2,6-dioxopiperidin-3-yl)-4-nitroisoindoline-1,3-dione (10 mg, as 0.025 mmol), iron powder (5.7 mg, 0.10 mmol) and ammonium chloride (5.4 mg, 0.10 mmol) in EtOH (0.5 mL) was stirred at 80° C. for 16 hours. After diluted with DMSO then filtered through membrane filter, the filtrate was purified by reverse phase preparative HPLC to give the title compound (3.4 mg, 37%) as a pale yellow solid.

$^1$H NMR (500 MHz, DMSO-$d_6$) δ 10.95 (s, 1H), 7.44 (dd, J=8.4, 7.0 Hz, 1H), 7.27-7.16 (m, 5H), 6.98 (d, J=8.4 Hz, 1H), 6.90 (d, J=7.0 Hz, 1H), 6.51 (s, 2H), 3.76 (d, J=13.6 Hz, 1H), 3.42 (d, J=13.6 Hz, 1H), 2.85 (dt, J=14.3, 4.5 Hz, 1H), 2.46-2.38 (m, 2H), 1.97 (ddd, J=14.3, 10.3, 6.7 Hz, 1H). LC/MS RT 1.02 min, m/z 364.4 $[M+H]^+$.

Example 36: Isothermal Titration Calorimetry (ITC) Measurements

All calorimetric experiments were carried out using an Affinity ITC from TA Instruments (New Castle, Del.) equipped with an auto sampler in a buffer containing 20 mM HEPES, pH 7.5, 150 mM NaCl, 0.5 mM TCEP, and 2% DMSO at 25° C. 20 μM protein solution containing PRPK or Cereblon (CRBN) in the calorimetric cell was titrated with 200 μM of a test compound solution using 2 μL injection in 200 seconds intervals using a stirring speed at 125 rpm. Resulting isotherm was fitted with a single site model to yield thermodynamic parameters of ΔH, ΔS, stoichiometry, and Kd using NanoAnalyze software (TA instruments).

Compounds 12, 13, 22, and 30 were evaluated in the above test. Pomalidomide was also evaluated in the above test as a control. The results are summarized in Table 1 below.

TABLE 1

| Compounds | ITC/PRPK (Kd, μM) | ITC/CRBN (Kd, μM) |
|---|---|---|
| Pomalidomide | 5.2 ± 2.2 | 5.1 ± 2.8 |
| Compound 12 | 0.28 ± 0.08 | >1000 |
| Compound 13 | 1.9 ± 1.7 | 0.54 |
| Compound 22 | >1000 | >1000 |
| Compound 30 | 0.36 ± 0.07 | >1000 |

As shown in Table 1, Compounds 12, 13, and 30 exhibited Kd values lower than Pomalidomide in inhibiting PRPK activities, which demonstrates that these compounds are more potent PRPK inhibitors than Pomalidomide. In addition, the results in Table 1 show that Compounds 12, 13, and 30 are not CRBN inhibitors.

Other embodiments are in the following claims.

What is claimed is:

1. A compound of formula (I) or a salt thereof:

(I)

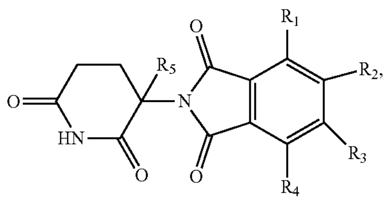

wherein at least one of each of $R_1$, $R_2$, $R_3$, and $R_4$, independently, is H, halo, OR, COOR, C (O) R, C(O)N(RR'), NH—S $(O)_2$—R, N (RR'), $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or R1 and R2, together with the carbon atoms to which they are attached, form a five-membered or six-membered ring; or $R_2$ and $R_3$, together with the carbon atoms to which they are attached, form a five-membered or six-membered ring; or $R_3$ and $R_4$, together with the carbon atoms to which they are attached, form a five-membered or six-membered ring; with the proviso that $R_1$ and $R_2$, or $R_2$ and $R_3$, or $R_3$ and $R_4$ forms a five-or six-membered ring;

$R_5$ is H or $C_1$-$C_{10}$ alkyl optionally substituted by aryl;

each of $C_1$-$C_{10}$ arylalkyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, five-membered ring, and six-membered, independently, is optionally substituted by $C_1$-$C_{10}$ alkyl, halo, OR, or COOR; and each of R and R', independently, is H, $C_1$-$C_{10}$ alkyl, $C_3$-$C_{20}$ cycloalkyl, $C_3$-$C_{20}$ heterocycloalkyl, aryl, or heteroaryl.

2. The compound of claim 1, wherein $R_1$ and $R_2$, together with the carbon atoms to which they are attached, form a five-membered or six-membered ring.

3. The compound of claim 2, wherein $R_1$ and $R_2$, together with the carbon atoms to which they are attached, form

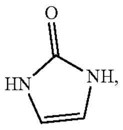,
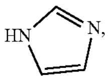,
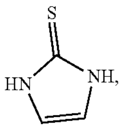,
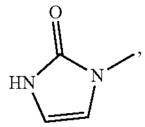,
or
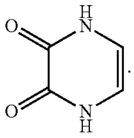.

4. Compounds 1-7 or a salt thereof:

| Compound No. | Structure | Name |
|---|---|---|
| 1 | 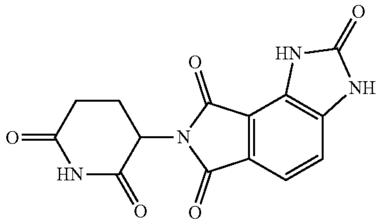 | 2-(2,6-dioxo-piperidin-3-yl)-5-(1H-pyrazol-4-yl) isoindoline-1,3-dione |
| 2 | 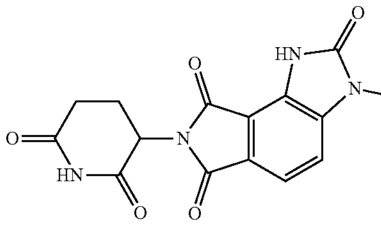 | 7-(2,6-dioxo-piperidin-3-yl)-3-methyl-1,3-dihydroimidazo [4,5-e]isoindole-2.6.8(7H)-trione |

-continued

| Compound No. | Structure | Name |
|---|---|---|
| 3 | 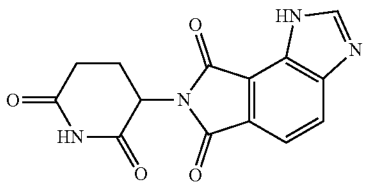 [SMILES: O=C1CCC(N2C(=O)c3ccc4nc[nH]c4c3C2=O)C(=O)N1] | 7-(2,6-dioxo-piperidin-3-yl) imidazo[4,5-e] isoindole-6,8 (1H,7H)-dione |
| 4 | 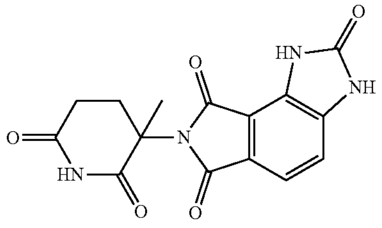 | 7-(3-methyl-2,6-dioxopiperidin-3-yl)-1,3-di-hydro-imidazo[4,5-e] isoindole-2,6,8(7H)-trione |
| 5 | 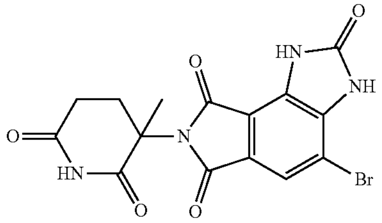 [SMILES: CC1(N2C(=O)c3cc(Br)c4[nH]c(=O)[nH]c4c3C2=O)CCC(=O)NC1=O] | 4-bromo-7-(3-methyl-2,6-dioxopiperidin-3-yl)-1,3-dihy-droimidazo[4,5-e]isoladole-2,6,8(7H)-trione |
| 6 | 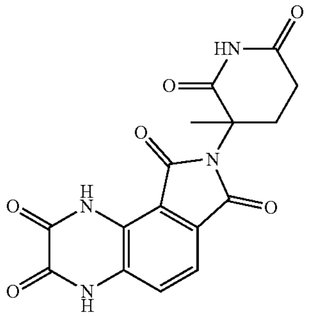 [SMILES: CC1(N2C(=O)c3ccc4[nH]c(=O)c(=O)[nH]c4c3C2=O)CCC(=O)NC1=O] | 8-(3-methyl-2,6-dioxopiperidin-3-yl)-1H-pyrrolo [3,4-f]quinexa-line-2,3,7,9(4H,8H)-tetraone |
| 7 | 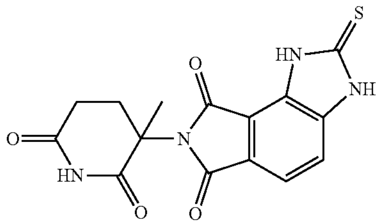 | 7-(3-methyl-2,6-dioxo-piperidin-3-yl)-2-thioxo-2,3-dihydroimidazo [4,5-e] isoindole-6,8(1H,7H)-di-one |

5. A pharmaceutical composition, comprising a compound of claim 1 and a pharmaceutically acceptable carrier.

6. A method for treating cancer in a subject in need thereof, comprising administering to the subject the pharmaceutical composition of claim 5 in an amount effective to treat the cancer.

7. A method of modulating PRPK activity in a cell, comprising contacting the cell in vitro with a compound of claim 1 in an amount sufficient to modulate PRPK activity.

8. A compound of formula (I) or a salt thereof:

(I)

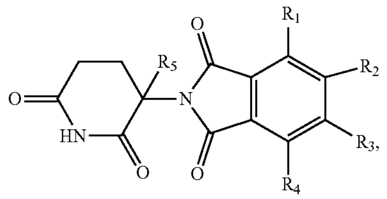

wherein each of $R_1$, $R_2$, $R_3$, and $R_4$, independently, is H, halo, OR, COOR, C(O)R, C(O)N (RR'), NH—$S(O)_2$—R, N(RR'), $C_1$-$C_{10}$ alkyl, $C_1$-$C_{10}$ arylalkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; provided that at least one of $R_1$, $R_2$, $R_3$, and $R_4$, independently, is NH—S $(O)_2$—R, $C_1$-$C_{20}$ heterocycloalkenyl, or heteroaryl;

$R_5$ is H or $C_1$-$C_{10}$ alkyl optionally substituted by aryl;

each of $C_1$-$C_{10}$ arylalkyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, five-membered ring, and six-membered ring, independently, is optionally substituted by $C_1$-$C_{10}$ alkyl, halo, OR, or COOR; and each of R and R', independently, is H, $C_1$-$C_{10}$ alkyl, $C_3$-$C_{20}$ cycloalkyl, $C_3$-$C_{20}$ heterocycloalkyl, aryl, or heteroaryl.

9. The compound of claim 8, wherein each of $R_1$ and $R_4$, independently, is H, OH, $OCH_3$, NH—$S(O)_2$-$CH_3$, $NH_2$,

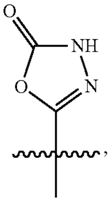, or 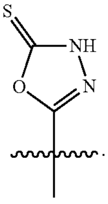.

10. The compound of claim 8, wherein each of $R_2$ and $R_3$, independently, is H, Br, OH, COOH, C(O)—(NH)—$CH_3$, $C(O)NH_2$, NH—$S(O)_2$—$CH_3$,

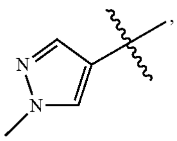, 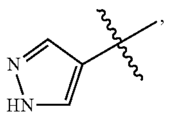, 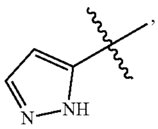,

-continued

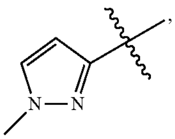, 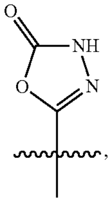, 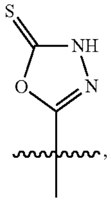, or

-continued

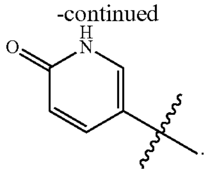.

11. The compound of claim 8, wherein the compound is one of Compounds 13-22, 28-34, or a salt thereof:

| | | |
|---|---|---|
| 13 | 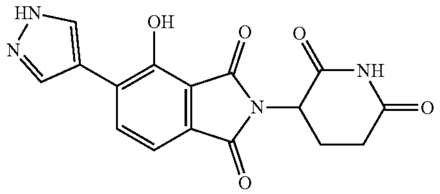 [SMILES: O=C1CCC(N2C(=O)c3ccc(-c4cn[nH]c4)c(O)c3C2=O)C(=O)N1] | 2-(2,6-dioxopiperidin-3-yl)-4-hydroxy-5-(1H-pyrazol-4-yl)isoindoline-1,3-dione |
| 14 | 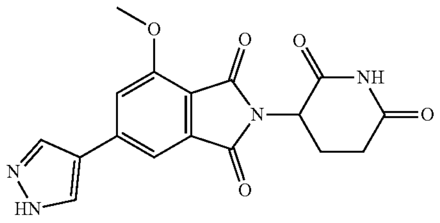 [SMILES: COc1cc(-c2cn[nH]c2)cc2c1C(=O)N(C1CCC(=O)NC1=O)C2=O] | 2-(2,6-dioxopiperidin-3-yl)-4-methoxy-6-(1H-pyrazol-4-yl)isoindoline-1,3-dione |
| 15 | 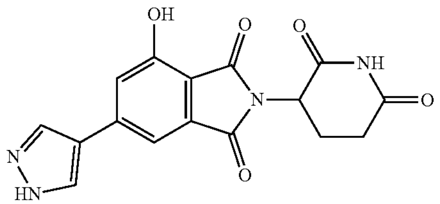 [SMILES: O=C1CCC(N2C(=O)c3cc(-c4cn[nH]c4)cc(O)c3C2=O)C(=O)N1] | 2-(2,6-dioxopiperidin-3-yl)-4-hydroxy-6-(1H-pyrazol-4-yl)isoindoline-1,3-dione |
| 16 | 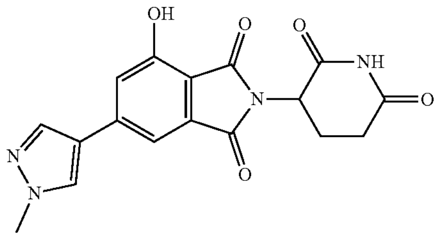 [SMILES: Cn1cc(-c2cc(O)c3c(c2)C(=O)N(C2CCC(=O)NC2=O)C3=O)cn1] | 2-(2,6-dioxopiperidin-3-yl)-4-hydroxy-6-(1-methyl-1H-pyrazol-4-yl)isoindoline-1,3-dione |
| 17 | 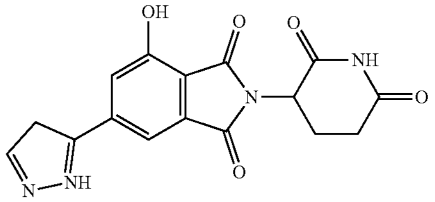 [SMILES: O=C1CCC(N2C(=O)c3cc(C4=NN=CC4)cc(O)c3C2=O)C(=O)N1] | 2-(2,6-dioxopiperidin-3-yl)-4-hydroxy-6-(1H-pyrazol-5-yl)isoindoline-1,3-dione |
| 18 | 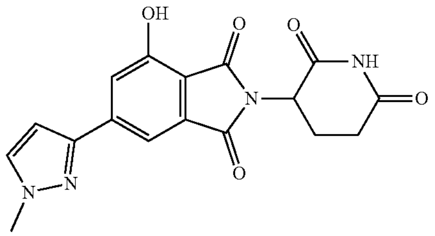 [SMILES: Cn1ccc(-c2cc(O)c3c(c2)C(=O)N(C2CCC(=O)NC2=O)C3=O)n1] | 2-(2,6-dioxopiperidin-3-yl)-4-hydroxy-6-(1-methyl-1H-pyrazol-3-yl)isoindoline-1,3-dione |

-continued

19 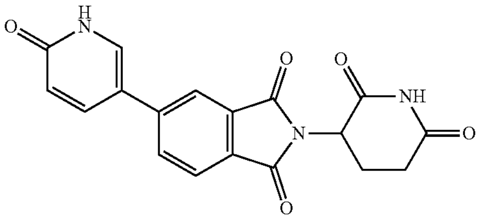 [SMILES: O=C1CCC(N2C(=O)c3ccc(-c4ccc(=O)[nH]c4)cc3C2=O)C(=O)N1]

2-(2,6-dioxopiperidin-3-yl)-5-(6-oxo-1,6-dihydropyridin-3-yl)isoindoline-1,3-dione 20 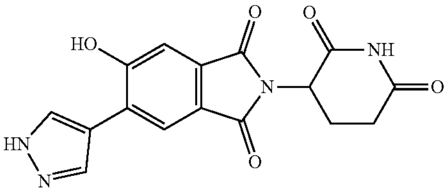 [SMILES: O=C1CCC(N2C(=O)c3cc(O)c(-c4cn[nH]c4)cc3C2=O)C(=O)N1]

2-(2,6-dioxopiperidin-3-yl)-5-hydroxy-6-(1H-pyrazol-4-yl)isoindoline-1,3-dione

21 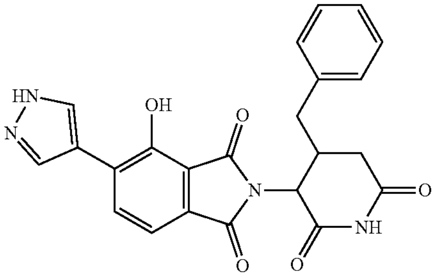 [SMILES: O=C1CC(Cc2ccccc2)C(N2C(=O)c3ccc(-c4cn[nH]c4)c(O)c3C2=O)C(=O)N1]

2-(3-benzyl-2,6-dioxopiperidin-3-y)-4-hydroxy-5-(1H-pyrazol-4-yl)isoindoline-1,3-dione 22 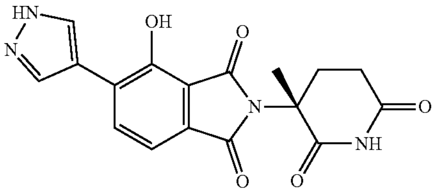 [SMILES: C[C@@]1(N2C(=O)c3ccc(-c4cn[nH]c4)c(O)c3C2=O)CCC(=O)NC1=O]

(R)-4-hydroxy-2-(3-methyl-2,6-dioxopiperidin-3-yl)-5-(1H-pymazo]-4-yl)isoindoline-1,3-dione 28 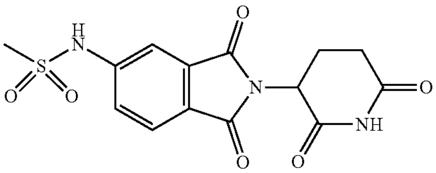 [SMILES: CS(=O)(=O)Nc1ccc2c(c1)C(=O)N(C1CCC(=O)NC1=O)C2=O]

N-(2-(2,6-dioxopiperidin-3-yl)-1,3-dioxoisoindolin-5-yl)methanesulfonamide

29 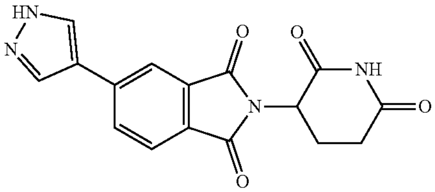 [SMILES: O=C1CCC(N2C(=O)c3ccc(-c4cn[nH]c4)cc3C2=O)C(=O)N1]

2-(2,6-dioxopiperidin-3-yl)-5-(1H-pyrazol-4-yl)isoindoline-1,3-dione

30 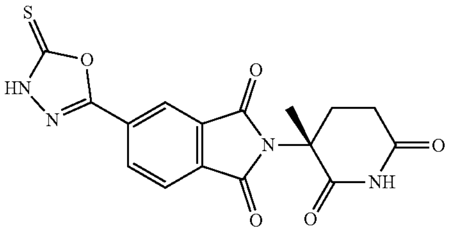 [SMILES: C[C@@]1(N2C(=O)c3ccc(-c4n[nH]c(=S)o4)cc3C2=O)CCC(=O)NC1=O]

(R)-2-(3-methyl-2,6-dioxopiperidin-3-yl)-5-(5-thioxo-4,5-dihydro-1,3,4-oxadiazol-2-yl)isoindoline-1,3-dione -continued

| | | |
|---|---|---|
| 31 | 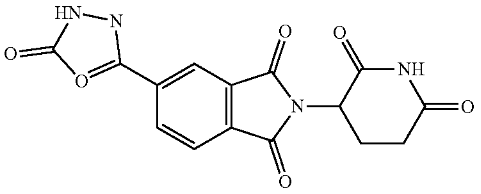 | 2-(2,6-dioxopiperidin-3-yl)-5-(5-oxo-4,5-dihydro-1,3,4-oxadiazol-2-yl)isoindoline-1,3-dione |
| 32 | 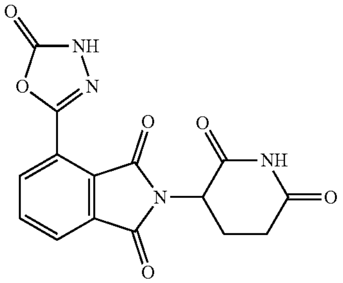 [SMILES: O=C1CCC(N2C(=O)c3cccc(-c4n[nH]c(=O)o4)c3C2=O)C(=O)N1] | 2-(2,6-dioxopiperidin-3-y1)-4-(5-oxo-4,5-dihydro-1,3,4-oxadiazol-2-yl)isoindoline-1,3-dione |
| 33 | 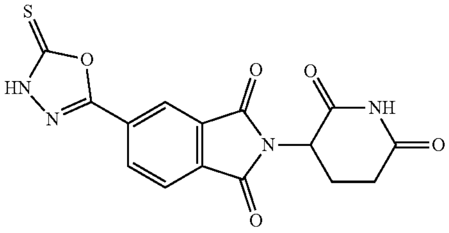 [SMILES: O=C1CCC(N2C(=O)c3ccc(-c4n[nH]c(=S)o4)cc3C2=O)C(=O)N1] | 2-(2,6-dioxopiperidin-3-yl)-5-(5-thioxo-4,5-dihydro-1,3,4-oxadiazol-2-ylisoindoline-1,3-dione |
| 34 | 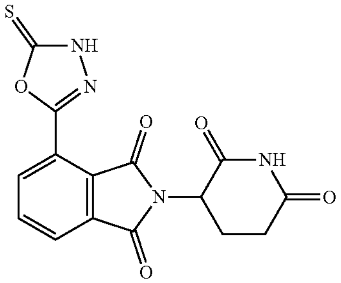 [SMILES: O=C1CCC(N2C(=O)c3cccc(-c4n[nH]c(=S)o4)c3C2=O)C(=O)N1] | 2-(2,6-dioxopiperidin-3-yl)-4-(5-thioxo-4,5-dihydro-1,3,4-oxadiazol-2-yl)isoindoline-1,3-dione |

12. A pharmaceutical composition, comprising a compound of claim 8 and a pharmaceutically acceptable carrier.

13. A method for treating cancer in a subject in need thereof, comprising administering to the subject the pharmaceutical composition of claim 12 in an amount effective to treat the cancer.

14. A method of modulating PRPK activity in a cell, comprising contacting the cell in vitro with a compound of claim 8 in an amount sufficient to modulate PRPK activity.

* * * * *